(12) United States Patent
Takata et al.

(10) Patent No.: US 9,314,213 B2
(45) Date of Patent: Apr. 19, 2016

(54) PRESS PLATE AND RADIOGRAPHIC IMAGING APPARATUS

(71) Applicant: FUJIFILM CORPORATION, Tokyo (JP)

(72) Inventors: Kenji Takata, Kanagawa (JP); Shinji Otokuni, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 142 days.

(21) Appl. No.: 14/033,868

(22) Filed: Sep. 23, 2013

(65) Prior Publication Data

US 2014/0093033 A1 Apr. 3, 2014

(30) Foreign Application Priority Data

Sep. 28, 2012 (JP) .................. 2012-218264

(51) Int. Cl.
*A61B 6/04* (2006.01)
*A61B 6/00* (2006.01)

(52) U.S. Cl.
CPC ............. *A61B 6/04* (2013.01); *A61B 6/0414* (2013.01); *A61B 6/4035* (2013.01); *A61B 6/488* (2013.01); *A61B 6/502* (2013.01); *A61B 6/0442* (2013.01); *A61B 6/4417* (2013.01); *A61B 6/542* (2013.01)

(58) Field of Classification Search
USPC ........................ 378/1, 37, 177, 208
See application file for complete search history.

(56) References Cited

U.S. PATENT DOCUMENTS

| | | | |
|---|---|---|---|
| 2008/0080668 A1 | 4/2008 | Kashiwagi | |
| 2014/0093034 A1* | 4/2014 | Takata et al. | 378/37 |

FOREIGN PATENT DOCUMENTS

| | | |
|---|---|---|
| JP | 2007-135704 A | 6/2007 |
| JP | 2008-86451 A | 4/2008 |
| JP | 2011-206438 A | 10/2011 |

OTHER PUBLICATIONS

Extended European Search Report dated Mar. 11, 2014.
Japanese Office Action dated Aug. 26, 2014, with English Translation thereof.
United States Office Action dated Apr. 8, 2015 in co-pending U.S. Appl. 14/033,899.
United States Office Action dated Aug. 28, 2015 in co-pending U.S. Appl. No. 14/033,899.

* cited by examiner

*Primary Examiner* — Nicole Ippolito
*Assistant Examiner* — Hanway Chang
(74) *Attorney, Agent, or Firm* — McGinn IP Law Group PLLC

(57) ABSTRACT

A press plate includes: a press section that is disposed to face towards an imaging face of an imaging table and is resiliently deformable; and a movable support point portion that is movable and supports the press section at the opposite side to the imaging face so that a reaction force occurring at the press section is adjusted according to a position of the movable support point portion to support the press section. The press plate may further include: a support section that is disposed separated from the press section on the opposite side to the imaging face and with at least one end portion coupled to one end portion of the press section, wherein the movable support point portion is movable between the press section and the support section so that a deformation amount of the press section is adjusted by such movement.

16 Claims, 17 Drawing Sheets

US 9,314,213 B2

PRESS PLATE AND RADIOGRAPHIC IMAGING APPARATUS

CROSS-REFERENCE TO RELATED APPLICATION

This application claims priority under 35 USC 119 from Japanese Patent Application No. 2012-218264 filed on Sep. 28, 2012, the disclosure of which is incorporated by reference herein.

BACKGROUND OF THE INVENTION

1. Technical Field

The present invention relates to a press plate and a radiographic imaging apparatus, and in particular to a press plate for performing image capture with an image capture body in a compressed state, and to a radiographic imaging apparatus provided with such a press plate.

2. Related Art

Mammography equipment for early detection of breast cancer and the like are known as medical radiographic imaging apparatuses. In mammography equipment, the breast of an examinee is interposed as an image capture body between an imaging face of an imaging table and a press plate, and then a radiographic image is captured with the breast in a pressed state by the press plate. Adopting such an imaging method makes the thickness of the image capture body thinner, and so enables a clear radiographic image to be obtained and enables the radiation amount to be reduced.

In Japanese Patent Application Laid-Open (JP-A) No. 2011-206438, a radiographic imaging apparatus and a press plate for a radiographic imaging apparatus are described that enable the burden on an examinee during breast pressing, and in particular the pain felt by the examinee, to be reduced. The press plate is equipped with a flexible press plate section that presses the breast against the imaging face of an imaging table, a reinforcement plate section that is integrally formed at both ends of the press plate section, and a support plate section that spans across the reinforcement plate section and maintains a gap to the press plate section.

SUMMARY

According to an aspect of the present disclosure, a press plate of the present invention includes: a press section that is disposed to face towards an imaging face of an imaging table and is resiliently deformable; and a movable support point portion that is movable and supports the press section at the opposite side of the press section to the imaging face such that a reaction force occurring at the press section is adjusted according to a position of the movable support point portion to support the press section.

BRIEF DESCRIPTION OF THE DRAWINGS

Exemplary embodiments of the present invention will be described in detail based on the following figures, wherein.

DETAILED DESCRIPTION OF THE INVENTION

Figure 1:
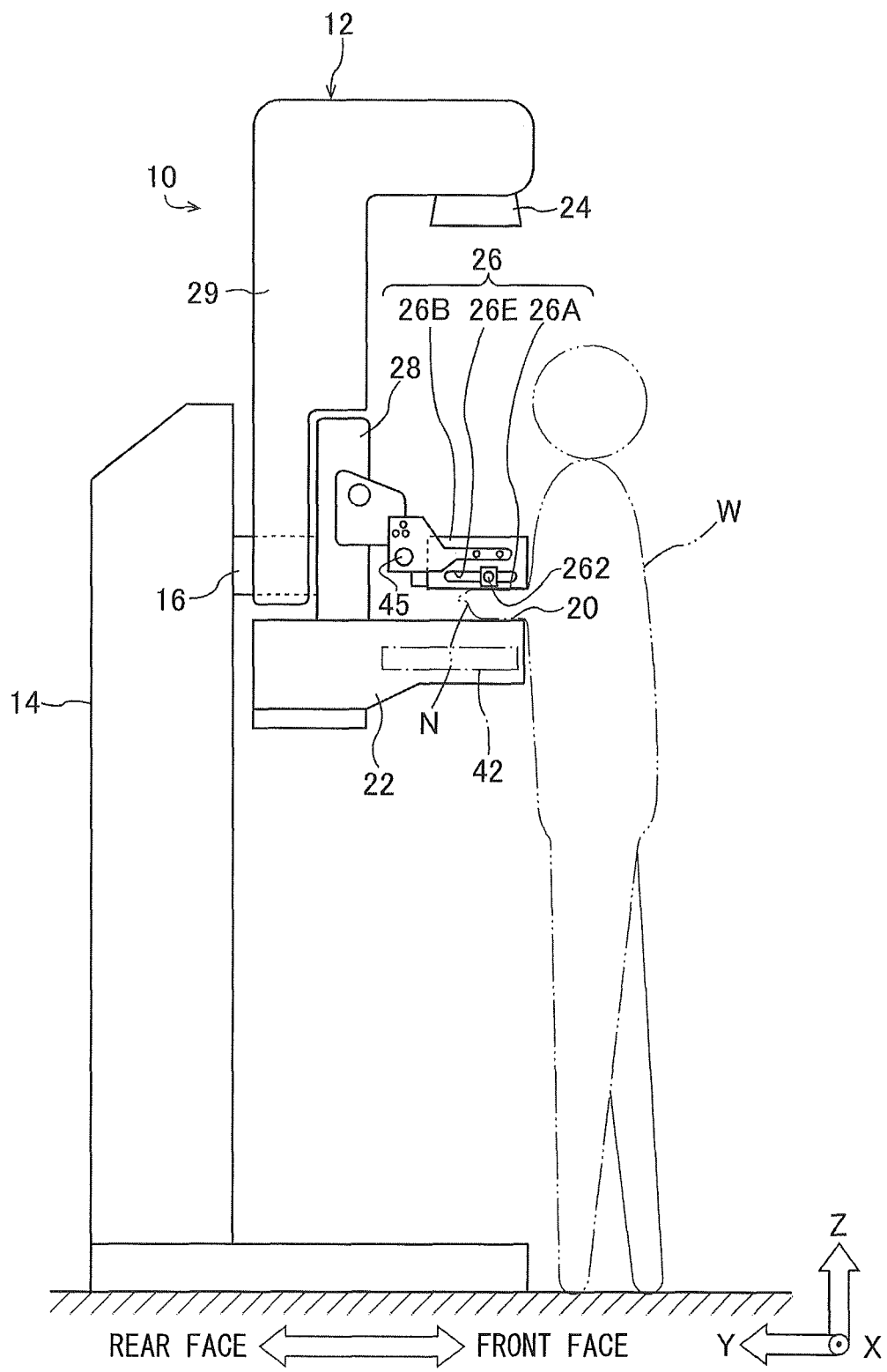
FIG. 1 is a schematic side view illustrating an overall configuration of a radiographic imaging apparatus according to a first exemplary embodiment of the present invention.

Explanation follows regarding exemplary embodiments of the present invention, with reference to the attached drawings. Note that configuration elements having similar functions are allocated the same reference numerals in the drawings, and duplicated explanation thereof is omitted as appropriate. As appropriate, the direction denoted by X in the drawings illustrates the direction from the right side towards the left side as viewed by an examinee (imaging subject) who is in a state oriented facing towards a radiographic imaging apparatus for radiographic imaging. Similarly, the direction denoted by Y in the drawings illustrates the direction from the front side of the examinee towards the rear face of the radiographic imaging apparatus, and the direction denoted by Z in the drawings illustrates the direction from the side below the feet of the examinee towards the upper side of the radiographic imaging apparatus.

First Exemplary Embodiment

In a first exemplary embodiment of the present invention, an example will be explained in which the present invention is applied to mammography equipment as a radiographic imaging apparatus, and to a press plate incorporated therein.

Overall Configuration of Radiographic Imaging Apparatus

As illustrated in FIG. 1, the radiographic imaging apparatus 10 according to the first exemplary embodiment is mammography equipment. The radiographic imaging apparatus 10 is configured to capture an image of a breast (image capture body) N of an examinee W using radiation while the examinee W is in an upright state. Note that the radiographic imaging apparatus 10 is capable of separately imaging the left and right breast N of the examinee W who is in a seated state on a seat such as a wheelchair, wherein only the upper body of the examinee W is in an upright state.

The radiographic imaging apparatus 10 is equipped with an imaging section 12 that is substantially C-shaped in side view and is provided at a front face (examinee W) side, and a base section 14 that is disposed further towards the Y direction (rear face) side than the imaging section 12 and supports the imaging section 12 from the rear face. The imaging section 12 is equipped from the lower side to the upper side with: an imaging table 22; a holder 28; a press plate 26; and a support section 29. The imaging table 22 is equipped with an imaging face 20 that makes contact with the breast N of the examinee W. In this case the shape of the imaging face 20 is rectangular in plan view, although there is no particular limitation to the shape thereof. From the perspectives of radiation permeability and mechanical strength, at least the imaging face 20 is formed from for example a carbon fiber reinforced plastic. The imaging table 22 is supported at the lower side of the holder 28, and the press plate 26 is supported by the holder 28 further to the upper side than the imaging table 22.

The press plate 26 is configured to interpose the breast N between itself and the imaging face 20, and to compress the breast N. The shape of the press plate 26 is rectangular-shaped in plan view, and is configured such as a rectangular box shape with a certain thickness along the Z direction. The press plate 26 is configured movable in the vertical direction with respect to the imaging face 20 (the Z direction in FIG. 1) so as to compress the breast N in a parallel state with respect to the imaging face 20. The press plate 26 is also configured rotatable about rotation supports points 45 provided between the press plate 26 and the holder 28, so as to be capable of compressing the breast N while supported at an angle with respect to the imaging face 20 (capable of tilted compressing). Namely, pain caused to the examinee W can be reduced during breast N compression due to the press plate 26 being held tilted about the rotation supports points 45 so as to widen out towards the base side of the breast N. Although not illustrated in the drawings, an angle detection sensor is provided at the rotation supports points 45, or in the vicinity thereof, to detect the compression tilt angle. Note that a detailed explanation regarding the construction of the press plate 26 and regarding the operation of the press plate 26 is given later.

The support section 29 is provided above the holder 28 as a separate component to the holder 28 and is configured shaped in a substantially inverted L-shape in side view. A radiation irradiation section 24 is provided at the upper side of the support section 29, facing towards the imaging face 20, and capable of irradiating radiation for imaging or for measurement.

As illustrated in FIG. 1, a rotation shaft 16 is provided at the upper side of the base section 14 so as to project out in a horizontal direction towards the apparatus front face side, and the support section 29 and the holder 28 are attached to the rotation shaft 16. Namely, the imaging section 12, including the support section 29, is rotatable with respect to the base section 14 about the rotation shaft 16.

It is also possible to switch between the coupled state of the rotation shaft 16 and the holder 28 together, or the uncoupled state of the rotation shaft 16 and the holder 28. In order to incarnate the such switching, for example, a gear wheel is provided to the rotation shaft 16 and the holder 28 that is switchable between a meshed state and an unmeshed state. In the coupled state, the holder 28 rotates accompanying rotation of the rotation shaft 16, and in the uncoupled state, the holder 28 is free to rotate with respect to rotation of the rotation shaft 16. The rotational force of the rotation shaft 16 is transmitted from a drive source provided inside the base section 14, not illustrated in the drawings.

Configuration of Radiation Irradiation Section

Figure 2:
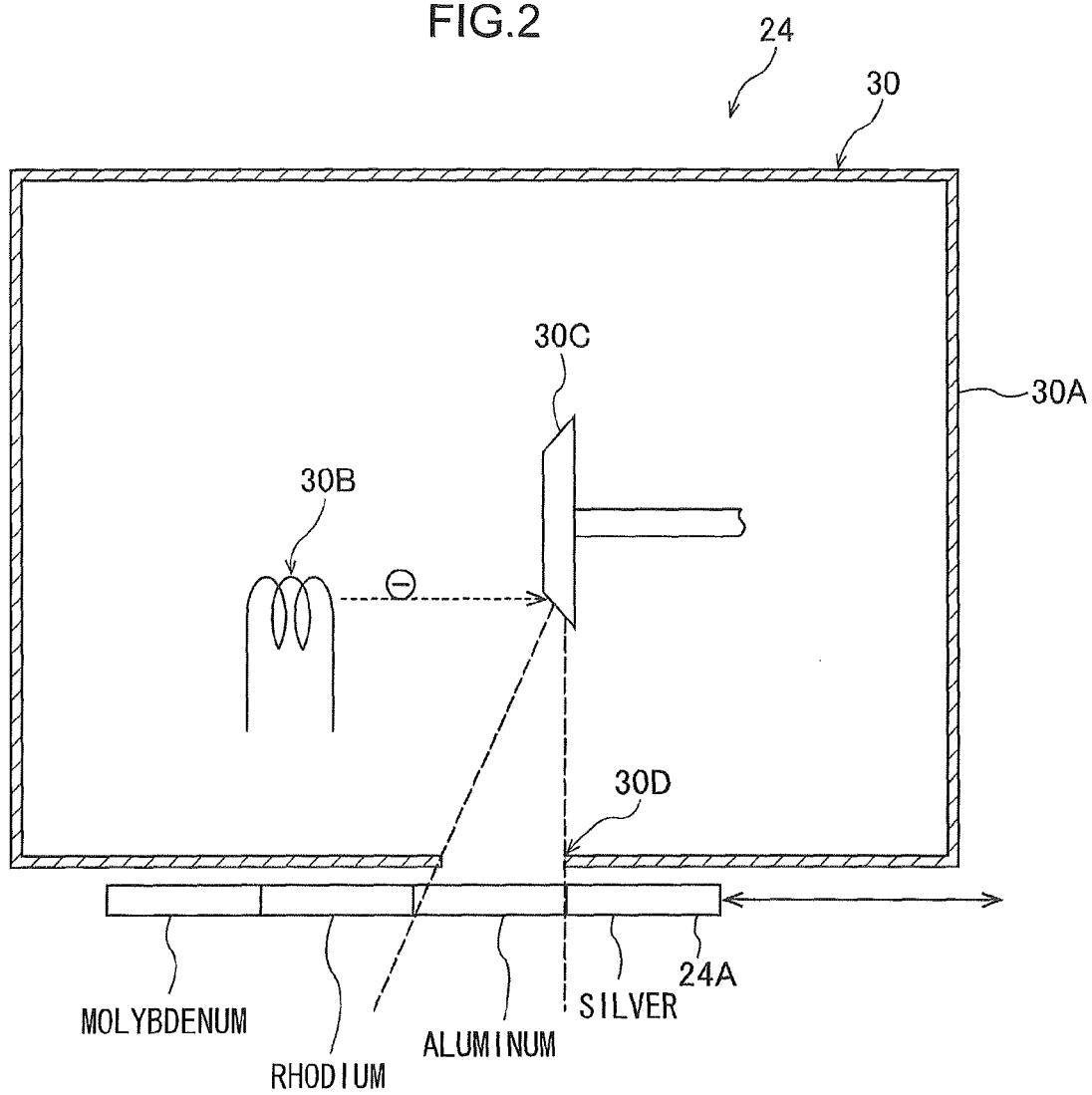
FIG. 2 is a schematic cross-section of a radiation irradiation section of the radiographic imaging apparatus illustrated in FIG. 1.

As illustrated in FIG. 2, the radiation irradiation section 24 is equipped with a radiation source 30 and a filter 24A. The radiation source 30 is equipped with a casing 30A, and is internally provided therein with a cathode 30B including a filament and an anode 30C used as a target. Thermions are emitted from the cathode 30B, the thermions are accelerated by the potential difference between the cathode 30B and the anode 30C, and are focused on and impact with the anode 30C. Bremsstrahlung is generated thereby. In the present case bremsstrahlung X-rays are emitted from the radiation irradiation section 24. Although not illustrated in the drawings, in the radiographic imaging apparatus 10 according to the first exemplary embodiment, there are plural individual radiation sources 30 provided, with different types of metal employed as the anode 30C for each of the plural individual radiation sources 30. Examples of metals that may be employed as the anode 30C include tungsten, molybdenum, and rhodium. The intensity of the bremsstrahlung emitted from the anode 30C differs according to the different types of metal.

Bremsstrahlung emitted from the radiation source 30 (sometimes simply referred to below as "radiation") passes through a window 30D provided in a lower wall (in this case a bottom section) of the casing 30A, then passes through the filter 24A provided at the outside of the window 30D, and is irradiated towards the imaging face 20. The filter 24A is, for example, a structure in which films of molybdenum, rhodium, aluminum and silver are joined sequentially along their film face direction. In the radiographic imaging apparatus 10 according to the first exemplary embodiment, the filter 24A is configured so as to be movable, for example, along the guide rail, not illustrated in the drawings, such that one of the metals of the filter 24A is disposed facing towards the window 30D. Namely, the radiation emitted from the window 30D passes through the changeable metal of the filter 24A, so as to enable irradiation towards the imaging face 20, enabling the characteristics of the radiation to be changed as appropriate.

Configuration of Radiation Detector

As illustrated in FIG. 1, a radiation detector 42 is internally provided to the imaging table 22. In the radiation detector 42, irradiated radiation from the radiation irradiation section 24, that has passed through the press plate 26, the breast N and the imaging face 20, and has picked up image data of the breast N, is received and the image data is detected. This image data is output to a storage section 47 (see FIG. 4), and stored as radiographic image data of the breast N in the storage section 47. A Flat Panel Detector (FPD) that converts radiation into a digital signal is, for example, is employed in the radiation detector 42.

In the radiation detector 42 according to the first exemplary embodiment, an indirect-conversion-type detector is employed in which radiation is first converted into light using a scintillator, not illustrated in the drawings, and then the converted light is converted into charges. Note that there is no limitation to an indirect-conversion-type detector, and a direct-conversion-type detector may be employed for the radiation detector 42, in which radiation is directly converted into charges in a semiconductor layer, and the charges are accumulated.

Figure 3:
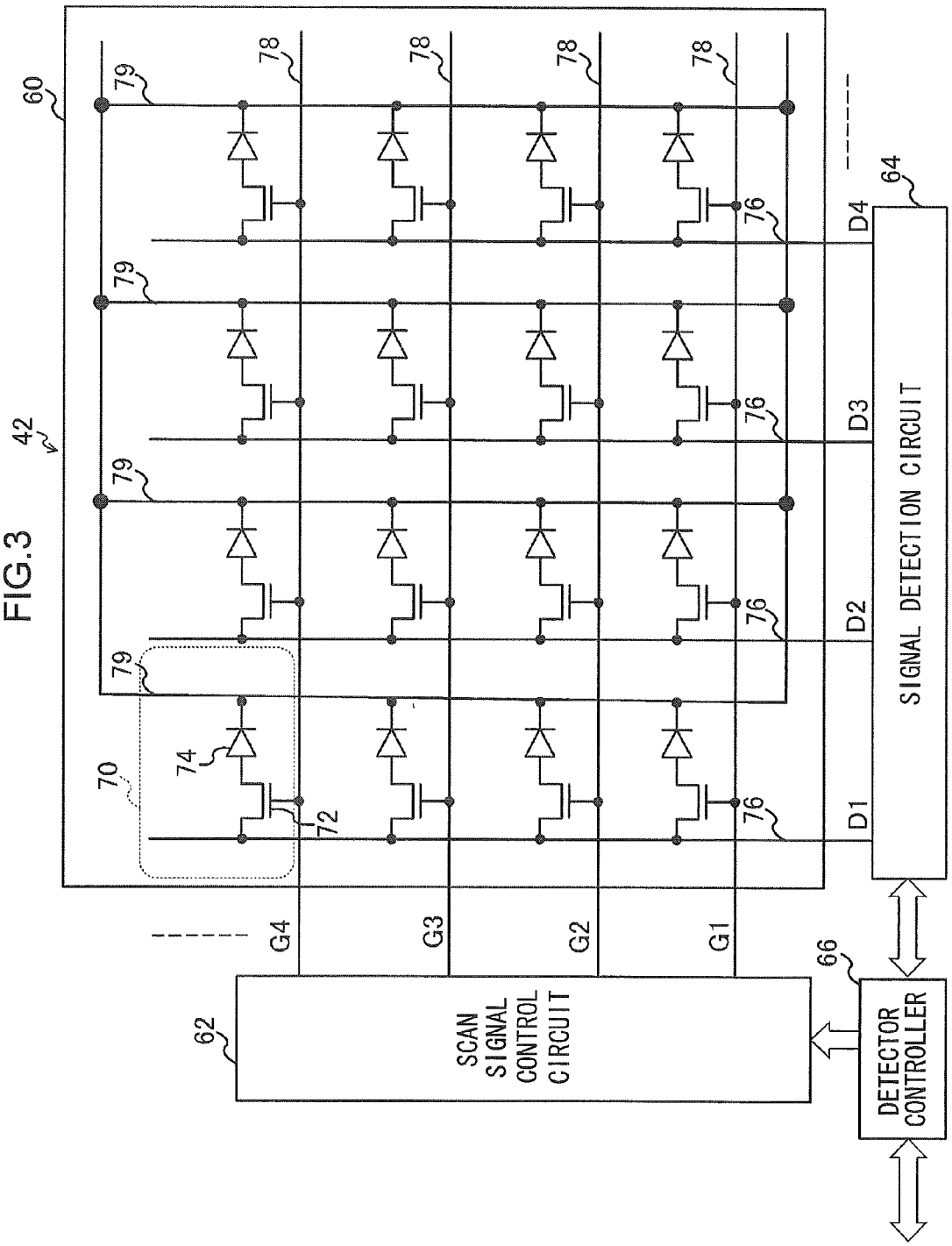
FIG. 3 is a block circuit diagram of a radiation detector of the radiographic imaging apparatus illustrated in FIG. 1.

As illustrated in FIG. 3, the radiation detector 42 has a detection section 60 with plural individual detection elements (pixels) 70 arrayed. Each of the detection elements 70 has a serial circuit of a photoelectric conversion portion 74 that generates charges on receipt of light converted from radiation and accumulate the charges, and a switching element 72 that reads out the charges accumulated in the photoelectric conversion portion 74. A photodiode may, for example, be employed as the photoelectric conversion portion 74. A Thin Film Transistor (TFT) is employed as the switching element 72.

Plurality of the detection elements 70 are arrayed, in a matrix form, along a direction of extension of scan signal lines 78 (for example a row direction), and along a direction of extension of output signal lines 76 that intersect with the scan signal lines 78 (for example a column direction). The scan signal lines 78 and the output signal lines 76 are provided on a substrate, not illustrated in the drawings. Each individual detection element 70 is disposed on the substrate at an intersection portion of one of the scan signal lines 78 and one of the output signal lines 76, and is electrically connected respectively to the one scan signal line 78 and the one output signal line 76. The detection section 60 illustrated in FIG. 3 is simplified to suit the page area, and is arrayed with several individual detection elements 70, however in practice there may be, for example, 1024 individual detection elements 70 arrayed in the scan signal line 78 extension direction and 1024 individual detection elements 70 arrayed in the output signal line 76 extension direction.

Moreover, in the detection section 60 there are also plural common electrode lines 79, each of which is provided so as to extend parallel to the respective output signal lines 76, respectively. A fixed power supply is supplied to the common electrode lines 79, and the common electrode lines 79 are connected to the corresponding photoelectric conversion portions 74.

A scan signal control circuit 62 is connected to the scan signal lines 78, enabling scan signals from the scan signal control circuit 62 to be supplied to the scan signal lines 78. The switching element 72 of each of the detection elements 70 connected to each of the scan signal lines 78 is controlled to a conducting or non-conducting state in response to the supply, or the non-supply, of respective scan signals. In the detection elements 70, the current flows in the switching element 72 according to the charge amount accumulated in the photoelectric conversion portion 74 at times when the switching element 72 is controlled to the conducting state. The charge amount, and the current amount flowing according to the charge amount, is radiographic image data of the breast N.

A signal detection circuit 64 is connected to the output signal lines 76. The current flowing in the switching element 72 of each of the detection elements 70 is output, as an output electrical signal of the detection element 70, through the output signal lines 76 to the signal detection circuit 64. Amplifiers to amplify the output electrical signals and AD converters to convert analogue signals into digital signals, not illustrated in the drawings, are built in the signal detection circuit 64 for each of the output signal lines 76. Namely, in the signal detection circuit 64 the output electrical signals (analogue signals) input from the output signal lines 76 are amplified by the amplification circuits, and converted to digital signals by the AD converters.

A detector controller 66 is provided in the radiation detector 42, and the detector controller 66 is connected both to the scan signal control circuit 62 and to the signal detection circuit 64. In the detector controller 66, specific processing such as noise reduction is performed on the digital signals output form the signal detection circuit 64, and a control signal to control detection of output electrical signals is output to the signal detection circuit 64. In the detector controller 66, a control signal to control output of scan signals is also output to the scan signal control circuit 62. The detector controller 66 is equipped with a Central Processing Unit (CPU), Read Only Memory (ROM), Random Access Memory (RAM), and a non-volatile storage section such as flash memory. In the detector controller 66, image data that is a radiographic image of the breast N is generated based on the output electrical signals of the detection elements 70 output from the signal detection circuit 64, and this image data is output to the storage section 47 (see FIG. 4) of the radiographic imaging apparatus 10.

Note that in the radiation detector 42 illustrated in FIG. 3, one scan signal control circuit 62 and one signal detection circuit 64 is provided for the individual detection section 60. The scan signal control circuit 62 and the signal detection circuit 64 are however not limited to such a configuration, and two or more scan signal control circuits 62 and two or more signal detection circuits 64 may be provided for the individual detection section 60.

System Configuration of Radiographic Imaging Apparatus

Figure 4:
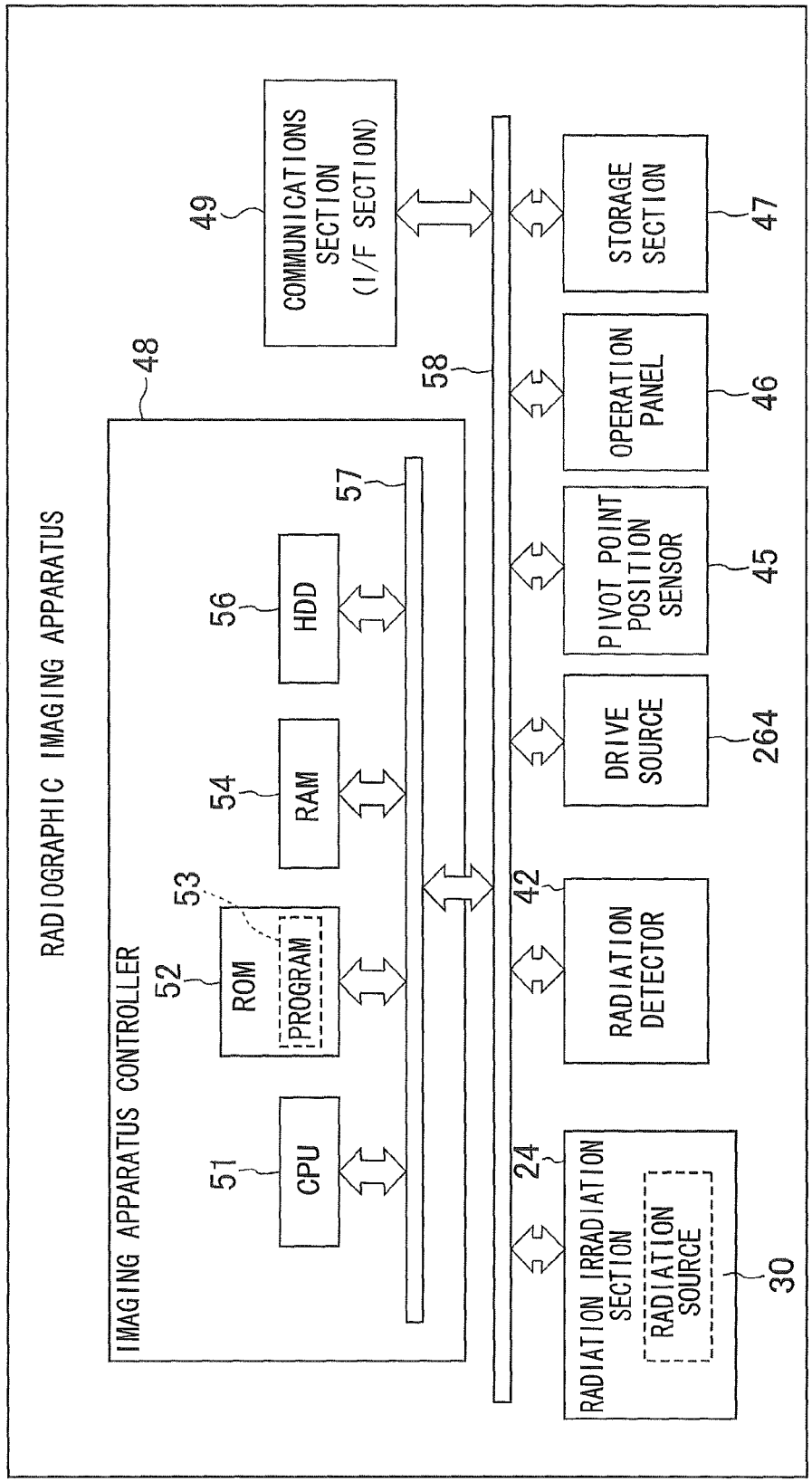
FIG. 4 is an overall system block diagram of the radiographic imaging apparatus illustrated in FIG. 1.

As illustrated in FIG. 4, the radiographic imaging apparatus 10 according to the first exemplary embodiment is equipped with an imaging apparatus controller 48, the radiation irradiation section 24, the radiation detector 42, an operation panel 46, the storage section 47, a communications section (I/F section) 49, a drive source 264 and a pivot point position sensor 45.

The imaging apparatus controller 48 is equipped with a CPU 51, ROM 52, RAM 54, and a Hard Disk Drive (HDD) 56. The CPU 51 and other sections are connected together by a common bus 57 such as a control bus or a data bus, thereby enabling transmission and reception of signals and the like between one another.

The CPU 51 performs overall control of the radiographic imaging apparatus 10. For example, when the CPU 51 has read in a program 53 stored on the ROM 52, the CPU 51 performs control of each section to implement the program 53. Note that although a configuration is given here in which the program 53 is pre-stored on ROM 52 there is no limitation thereto. For example, an external recording medium such as a CDROM or a removable device in which the program 53 is stored may be created, and then the program 53 may be installed from the external recording medium onto for example the ROM 52. Moreover, the program 53 may be installed from an external device via a communication line such as the internet onto the ROM 52 for example. The RAM 54 is employed as work space during execution of the program 53 by the CPU 51, and the program 53 is temporarily stored on the RAM 54. Various data such as radiographic image data is stored in the HDD 56. In the imaging apparatus controller 48, the radiation irradiation section 24, the radiation detector 42, the operation panel 46, the storage section 47, the communications section (I/F section) 49 and the drive source 264 are connected to one another through the internally provided common bus 57, an externally provided common bus 58 and the pivot point position sensor 45.

In the radiographic imaging apparatus 10, a radiation irradiation instruction is generated on operation of an exposure switch of the operation panel 46 by a user (operator). Following the radiation irradiation instruction, the imaging apparatus controller 48 executes an imaging procedure (the program 53) set based on the instructed exposure conditions, and the control of the irradiation of the radiation from the radiation irradiation section 24 towards the imaging face 20 is performed.

The operation panel 46 is an interface between the radiographic imaging apparatus 10 and the operator, is capable of performing for example input of various operation data such as exposure conditions and orientation data, and is capable of setting various operation instructions. Exposure conditions include at least data such as tube voltage, tube current, exposure time, and orientation data. For cases in which image capture is performed from plural directions with respect to the breast N, the orientation data includes at least data of imaging orientation and imaging position data such as imaging angle data. Note that the various operation data and various operation instruction data may be acquired from an external device or system, such as a system that manages data related to radiation-based medical consultation and radiation-based diagnosis, which is referred to as a Radiology Information System (RIS). Moreover, various operation data and various operation instruction data may be pre-stored on the HDD 56 of the imaging apparatus controller 48.

In the imaging apparatus controller 48, on input of the various operation data and the various operation setting instructions from the operation panel 46, an imaging procedure is executed based on the settings, radiation from the radiation irradiation section 24 is irradiated onto the breast N of the examinee W and a radiographic image is captured. In cases in which a radiographic image of the breast N is captured from above, the orientation of the holder 28 is adjusted such that the imaging face 20 is in an upwards facing state, and the orientation of the support section 29 is adjusted such that the radiation irradiation section 24 is positioned above and facing towards the imaging face 20. Moreover, in cases in which a radiographic image of the breast N is captured from the side, the orientation of the holder 28 is adjusted such that the imaging face 20 is in state facing towards the side, and the orientation of the support section 29 is adjusted such that the radiation irradiation section 24 is positioned to the side of and faces towards the imaging face 20. Such an adjustment is performed by the imaging apparatus controller 48.

The communications section 49 is employed as an interface that transmits radiographic image data stored for example in the storage section 47 of the radiographic imaging apparatus 10 to an external device (for example an external monitor), or receives data such as various operation data from an external device (for example RIS) or various operation instructions. In the communications section 49, there is no limitation to transmitting and receiving of data by wired technology and data may be transmitted and received using wireless technology.

Press Plate Configuration

Figure 5:
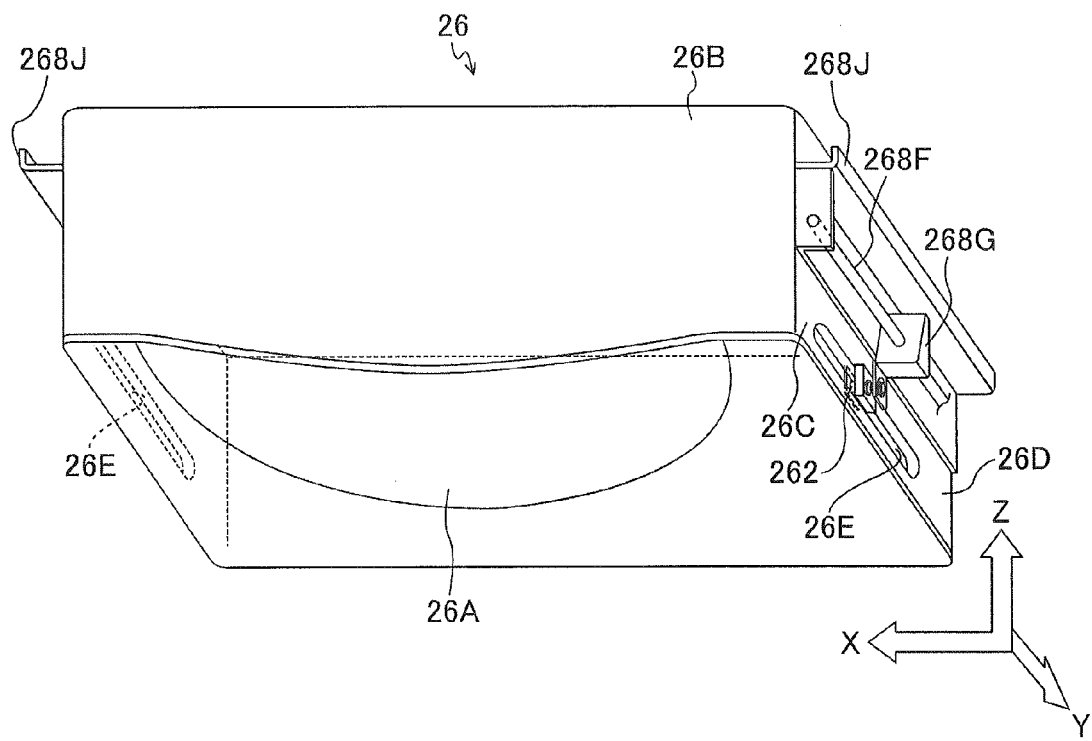
FIG. 5 is a perspective view from the front-face side of a press plate of the radiographic imaging apparatus illustrated in FIG. 1.
Figure 6:
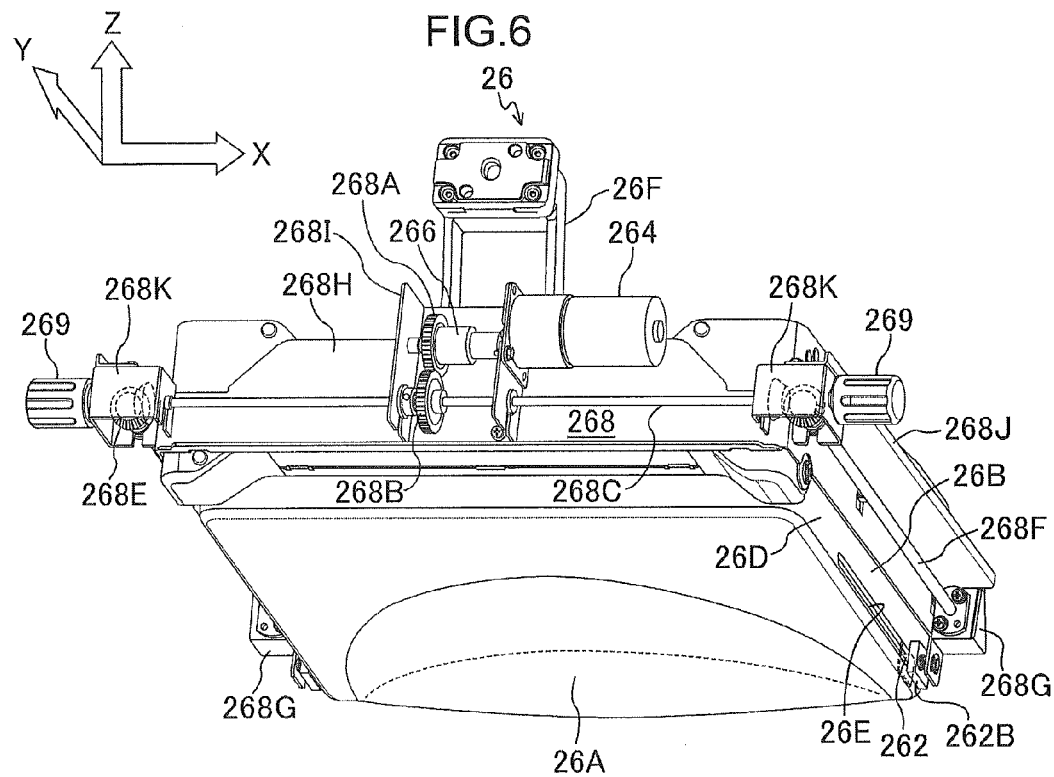
FIG. 6 is a perspective view from the back-face side of the press plate illustrated in FIG. 5.

As illustrated in FIG. 5 and FIG. 6, the box shaped press plate 26 incorporated in the radiographic imaging apparatus 10 according to the first exemplary embodiment is equipped with at least a press section 26A, a support section 26B, and a movable support point portion 262. The press section 26A is disposed facing towards the imaging face 20 of the imaging table 22, has a thickness that is thin in the Z direction and is configured elastically deformable. The support section 26B is disposed on the opposite side of the press section 26A to the imaging face 20 (in the Z direction in FIG. 5 and FIG. 6) and separated from the imaging face 20. Moreover, one end portion that is at the front face side of the support section 26B and one end portion that is at the front face side of the press section 26A are coupled together through a coupling section 26C, and another end portion that is at the rear face side of the support section 26B and another end portion that is at the rear face side of the press section 26A are coupled together through a coupling section 26D. The thickness in the Z direction of the support section 26B is set thicker than the thickness in the Z direction of the press section 26A, with the overall rigidity of the support section 26B higher than the overall rigidity of the press section 26A. Namely, the support section 26B is configured so as to be relatively more difficult to deform than the press section 26A. The movable support point portion 262 is movable in the Y direction in the first exemplary embodiment between the press section 26A and the support section 26B. By moving the movable support point portions 262 with respect to the press section 26A, the movable support point portions 262 change the position of support from the support section 26B to the press section 26A, so that a change in reaction force received by the press section 26A occurs when the press section 26A presses the breast (image capture body) N of the examinee W. The profile of the press section 26A can accordingly be changed, enabling the deformation amount of the press section 26A to be adjusted.

Figure 7:
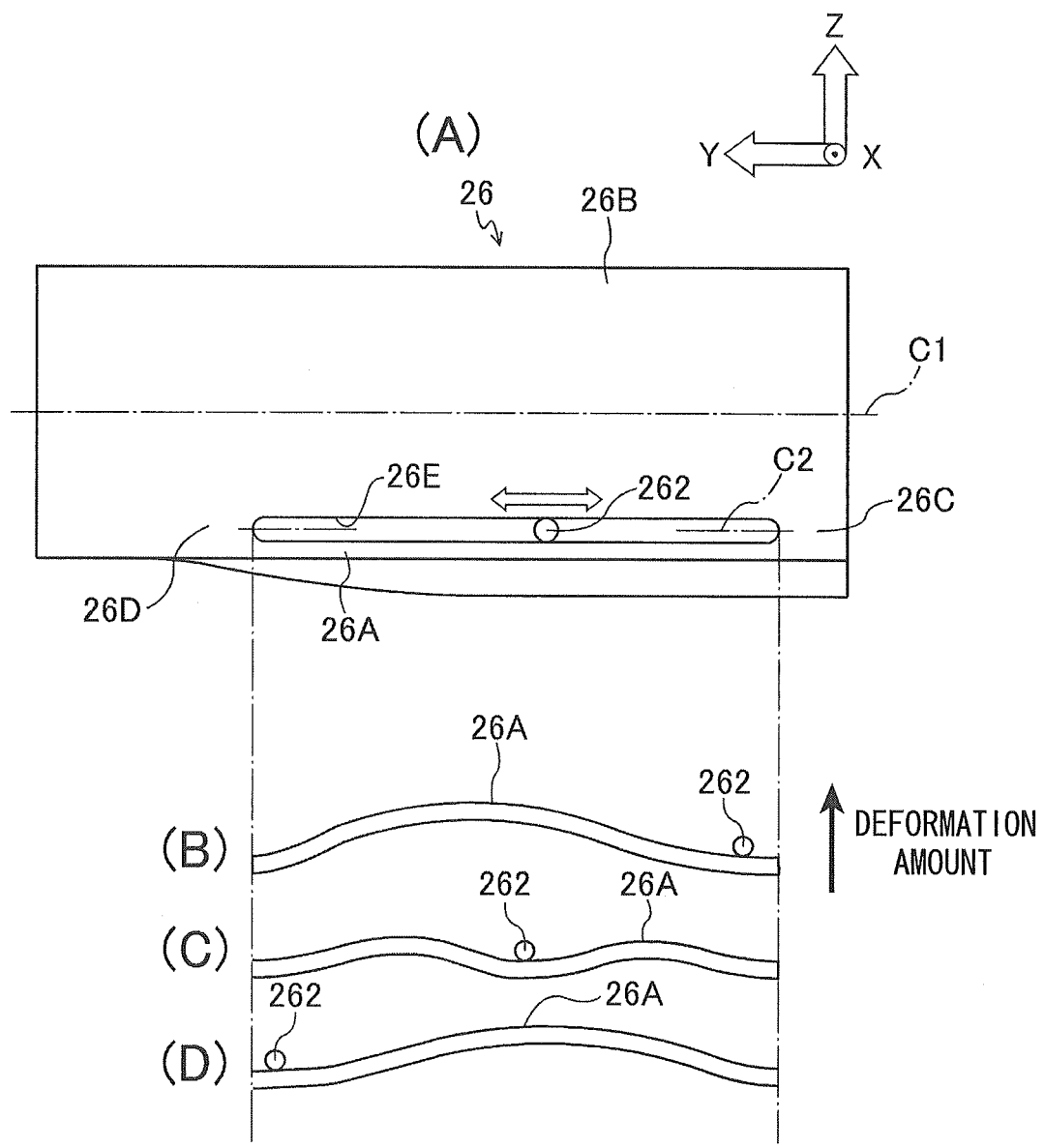
FIG. 7 is a schematic side view of the press plate illustrated in FIG. 5 and FIG. 6, and annotations B to D in FIG. 7 schematically illustrate deformation states of a press section corresponding to movement positions of a movable pivot point of the press plate.

The press plate 26 is configured in a hollow rectangular box shape, with a space present inside the press plate 26. A separation portion between the press section 26A and the support section 26B, and the movable support point portion 262 are both provided on both X direction facing side faces of the press plate 26 of the first exemplary embodiment. As illustrated in FIG. 5, FIG. 6 and FIG. 7, the press section 26A and the support section 26B are integrally formed through the coupling sections 26C and 26D. In other words, a slit 26E is provided to each of the side faces of the press plate 26, extending from a portion at one end side of the press section 26A and the support section 26B to span across to a portion at the other end side thereof, such that the press section 26A and the support section 26B are separated from each other but coupled together at both end portions. Since the press section 26A, the support section 26B, and the coupling sections 26C and 26D are integrally formed in the same material, as illustrated in FIG. 7, a central position C2 in the Z direction of the slit 26E is lower than a central position C1 in the Z direction of the press plate 26. Thus since they are of the same material, the overall rigidity of the support section 26B is higher, and the overall rigidity of the press section 26A is lower, in a configuration in which the press section 26A is easily deformed.

The press section 26A and the support section 26B of the press plate 26 are formed using a resin material with properties that allow easy transmission of the bremsstrahlung X-rays used here as the radiation. More specific examples of materials that may be employed as such resin materials include polycarbonate (PC), polyethylene terephthalate (PET), acrylates, and polypropylene (PP).

As illustrated at (A) of FIG. 7, the movable support point portion 262 is movable in the slit 26E in the press plate 26 along the Y direction that is the extension direction of the slit 26E. Namely, the length direction of the slit 26E matches the movement direction of the movable support point portion 262.

Schematic illustrations showing deformation states and deformation amounts of the press section 26A with respect to the movement position of the movable support point portion 262 are illustrated at (B) to (D) of FIG. 7. The movement position of the movable support point portion 262 illustrated in (B) is at the front face side (the examinee W side) of the press plate 26. In such cases, the press section 26A is supported at the front face side of the press plate 26 by the support section 26B though the movable support point portion 262, and so the deformation amount of the press section 26A is small. At an intermediate portion of the press plate 26, the press section 26A is not supported by the support section 26B, and so the deformation amount of the press section 26A is large. At the rear face side of the press plate 26, although the press section 26A is not supported by the support section 26B, the coupling section 26D is present, and so the deformation amount of the press section 26A is an intermediate amount. Note that the separation distance between the movable support point portion 262 and the coupling section 26D is long at the rear face side of the press plate 26, and the length of the press section 26A that is in a jutting out state in the Y direction is long, so the deformation amount of the press section 26A is quite large.

The movement position of the movable support point portion 262 illustrated in (C) is an intermediate portion of the press plate 26. In such cases, the press section 26A is supported at the intermediate portion of the press plate 26 by the support section 26B through the movable support point portion 262, and so the deformation amount of the press section 26A is small. At the front face side and the rear face side of the press plate 26, although the press section 26A is not supported by the support section 26B, the coupling sections 26C and 26D are present, and the length of the press section 26A jutting out in the Y direction is reduced by half by the support section 26B, and so the deformation amount of the press section 26A is an intermediate amount.

The movement position of the movable support point portion 262 illustrated in (D) is the rear face side of the press plate 26. In such cases, the press section 26A is supported at the rear face side of the press plate 26 by the support section 26B through the movable support point portion 262, and so the deformation amount of the press section 26A is small. Moreover, at an intermediate portion of the press plate 26, the press section 26A is not supported by the support section 26B and so the deformation amount of the press section 26A is large. At the front face side of the press plate 26, although the press section 26A is not supported by the support section 26B, the coupling section 26C is present, and so the deformation amount of the press section 26A is an intermediate amount. Note that at the front face side of the press plate 26, there is a long separation distance between the movable support point portion 262 and the coupling section 26C, and there is a long length of the press section 26A jutting out in the Y direction, and so the deformation amount of the press section 26A is quite large.

Namely, the length of the portion of the press section 26A that juts out in the Y direction and is not supported by the movable support point portion 262 depends on the distance from one end at the front face side of the slits 26E to the position to which the movable support point portion 262 has moved, or the distance from the other end at the rear face side of the slits 26E to the position to which the movable support point portion 262 has moved. The deformation amount of the press section 26A can accordingly be adjusted.

As illustrated in FIG. 5 and FIG. 6, one portion that is located at the front-face side of the press section 26A is configured with a local surface profile that projects out to the imaging face 20 side. Specifically, this portion of the press section 26A, has a circular arc shape in plan view, similar to the shape of the breast N, that widens out towards the front-face side and gradually narrows on progression towards the back-face side, with the projection amount decreases progressively from the front-face side towards the back-face side. Consequently, when the breast (image capture body) N, that is softer than the press section 26A and that has a local surface profile that projects out towards the press section 26A side, is interposed between the imaging face 20 and the press section 26A, a central portion of the breast N is pressed by the local surface profile of the press section 26A and the vicinity of the central portion is spread out. The thickness of the breast N interposed between the imaging face 20 and the press section 26A can thereby be made uniform. In the first exemplary embodiment, the press section 26A is configured such that the thickness of the breast N is made uniform by the local surface profile within a practical range of pressing force of 40N to 120N.

Figure 8:
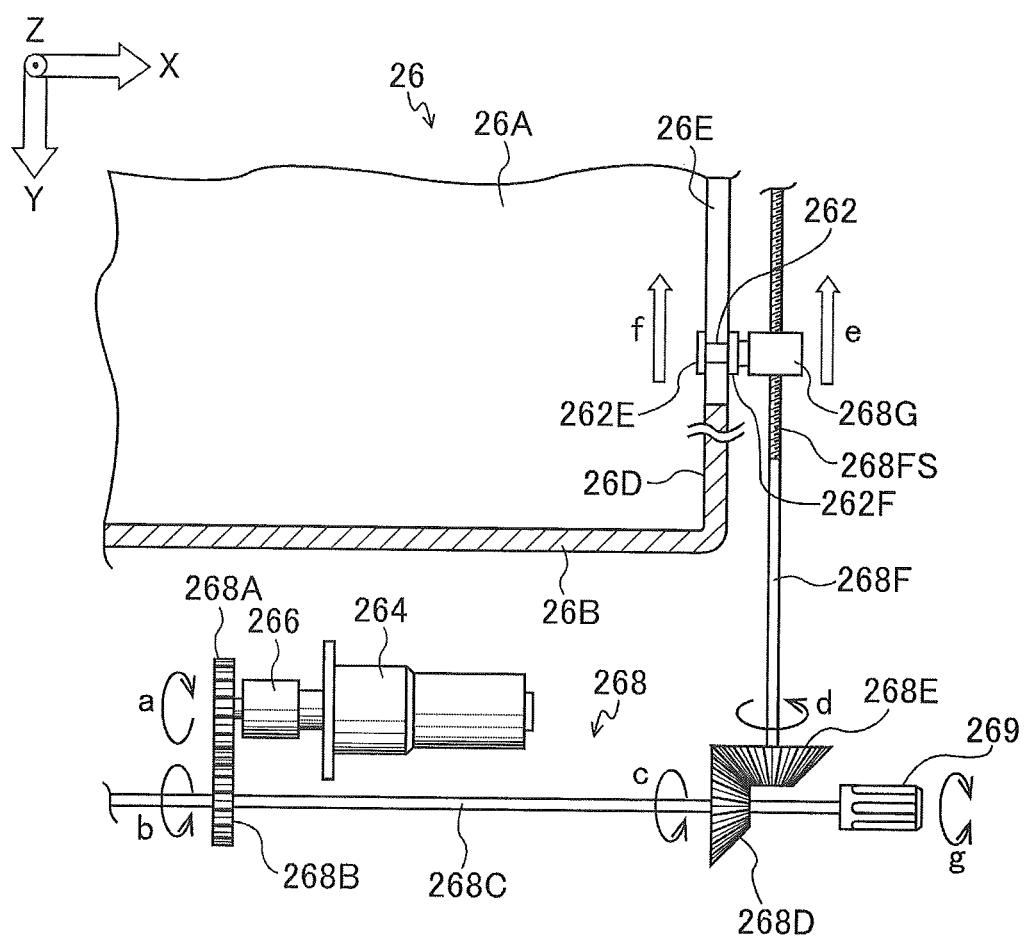
FIG. 8 is a schematic plan view of part of a drive source and a transmission mechanism of the press plate illustrated in FIG. 6 in plan view.

Configuration of Press Plate Drive Source and Configuration of Transmission Mechanism As illustrated in FIG. 5, FIG. 6 and FIG. 8, the press plate 26 according to the first exemplary embodiment is equipped with a drive source 264, and with a transmission mechanism 268 that transmits drive force of the drive source 264 to the movable support point portions 262. The movable support point portions 262 move inside the slits 26E according to the drive force transmitted from the drive source 264 to the transmission mechanism 268. An electrical motor may, for example, be employed as the drive source 264. The rotation axis (drive axis) direction of the electrical motor is oriented along the X direction in such a case. The drive source 264 is attached to support section 26B through a plate shaped bracket 268H that is attached to the rear face of the support section 26B and through a bracket 268I that is attached to a central portion of the bracket 268H and that is U-shaped in plan view open towards the outside.

The transmission mechanism 268 includes a gear wheel 268A, a gear wheel 268B, a rotation transmission shaft 268C, drive side bevel gears 268D, following side bevel gears 268E, rotation transmission shafts 268F, and movable portions 268G The gear wheel 268A of the transmission mechanism 268 is rotatably attached to the bracket 268I, and is rotated on receipt of drive force from the drive source 264. In the transmission mechanism 268, a clutch 266 is provided between the drive source 264 and the gear wheel 268A. The clutch 266 is capable of switching between a state in which drive force from the drive source 264 is transmitted to the gear wheel 268A, and a non-transmission state thereof. The gear wheel 268B is similarly rotatably attached to the bracket 268I, and is rotated on receipt of drive force transmitted from the gear wheel 268A. The rotation transmission shaft 268C is connected to a rotation shaft of the rotation axis of the gear wheel 268B, and is rotatably attached to the bracket 268I and brackets 268K, such that the drive force transmitted from the gear wheel 268B is received and rotates the rotation transmission shaft 268C. The rotation transmission shaft 268C extends at the rear face of the press plate 26 along the X direction to both side faces of the press plate 26, and the gear wheel 268B is connected to a central portion of the rotation transmission shaft 268C.

The drive side bevel gears 268D are fixed to the two ends of the rotation transmission shaft 268C, and the drive side bevel gears 268D rotate on receipt of drive force transmitted from the rotation transmission shaft 268C. The following side bevel gears 268E are rotatably attached to the brackets 268K, mesh with the drive side bevel gears 268D, and are rotated on receipt of drive force transmitted from the drive side bevel gears 268D. The transmission direction of drive force transmitted along the rear face of the support section 26B by the drive side bevel gears 268D and the following side bevel gears 268E changes by about 90° along the direction of the side face of the support section 26B. The rotation transmission shafts 268F are connected to the rotation shaft of the following side bevel gears 268E and rotate on receipt of drive force transmitted from the following side bevel gears 268E. As illustrated in FIG. 8, male threaded drive sections 268FS are provided to the rotation transmission shafts 268F in regions corresponding to the slits 26E. Although omitted in the drawings, female drive threaded sections that mesh with the male threaded drive sections 268FS are provided to the movable portions 268G. The drive force transmitted from the rotation transmission shafts 268F is transmitted to the movable portions 268G through the male threaded drive sections 268FS and the female drive threaded sections. The movable portions 268G are capable of moving along the male threaded drive sections 268FS, namely along the slits 26E. The movable support point portions 262 are connected to the movable portions 268G. Guide members 262E are provided on one end portion of the movable support point portions 262 that project out to the inside of the press plate 26, and guide members 262F are provided between the outside of the press plate 26 and the movable portions 268G. The movable support point portions 262 are capable of moving along the slits 26E, guided by the guide members 262E and the guide members 262F.

In the transmission mechanism 268, as illustrated in FIG. 8, when for example drive force (rotation) is transmitted in the a-arrow direction from the drive source 264 to the gear wheel 268A, the drive force is transmitted to the gear wheel 268B in the b-arrow direction that is the opposite direction to the a-arrow direction. This drive force is transmitted to the drive side bevel gears 268D through the rotation transmission shaft 268C as a drive force in an c-arrow direction that is the same direction as the b-arrow direction. The drive force of the drive side bevel gears 268D is transmitted to the following side bevel gears 268E as drive force in the d-arrow direction, and the drive force in the d-arrow direction is transmitted to the male threaded drive sections 268FS of the rotation transmission shafts 268F. As a result, the movable portions 268G are moved in the e-arrow direction from the rear face side of the press plate 26 towards the front face side, and the movable support point portions 262 move in the f-arrow direction accompanying movement of the movable portions 268G. Note that FIG. 8 illustrates a portion of the transmission mechanism 268 provided on the left side face of the press plate 26 as viewed from the examinee W. The basic configuration of the transmission mechanism 268 provided on the right side face of the press plate 26 is similar, however opposite-handed threads are provided to the male threaded drive sections 268FS and the female drive threaded sections to those on the left side face in order to make the movement direction of the movable support point portions 262 the same on both the left and right side faces.

Moreover, in order to detect the movement position of the movable support point portions 262, the pivot point position sensor 45 is provided to the press plate 26 as illustrated in FIG. 4. Although a detailed structure is not illustrated in FIG. 8, a sensor for detecting the drive amount of the drive source 264, or more specifically the number of rotations or rotation angle of an electric motor, a sensor for detecting the number of rotations or rotation angle of for example the gear wheel 268A, or a sensor for directly detecting the movement amount of the movable portions 268G or the movable support point portions 262, is employed as the pivot point position sensor 45.

Moreover, as illustrated in FIG. 6 and FIG. 8, in the press plate 26 according to the first exemplary embodiment, a manual adjustment section 269 is respectively coupled to the two ends of the rotation transmission shaft 268C of the transmission mechanism 268. The manual adjustment section 269 imparts a drive force to move the movable support point portions 262 that is separate to the drive force from the drive source 264. On a user imparting drive force in the g-arrow direction in FIG. 8 to the manual adjustment section 269, the movable support point portions 262 are moved along the slits 26E according to this drive force. Note that the coupled state between the drive source 264 and the gear wheel 268A is released by the clutch 266 at times when drive force is being imparted from the manual adjustment section 269. The coupled state is released because the drive source 264 would otherwise bear the load when drive force is imparted from the manual adjustment section 269, enabling easy movement of the movable support point portions 262 to be performed using the manual adjustment section 269.

Operation of Radiographic Imaging Apparatus and Press Plate

Figure 9:
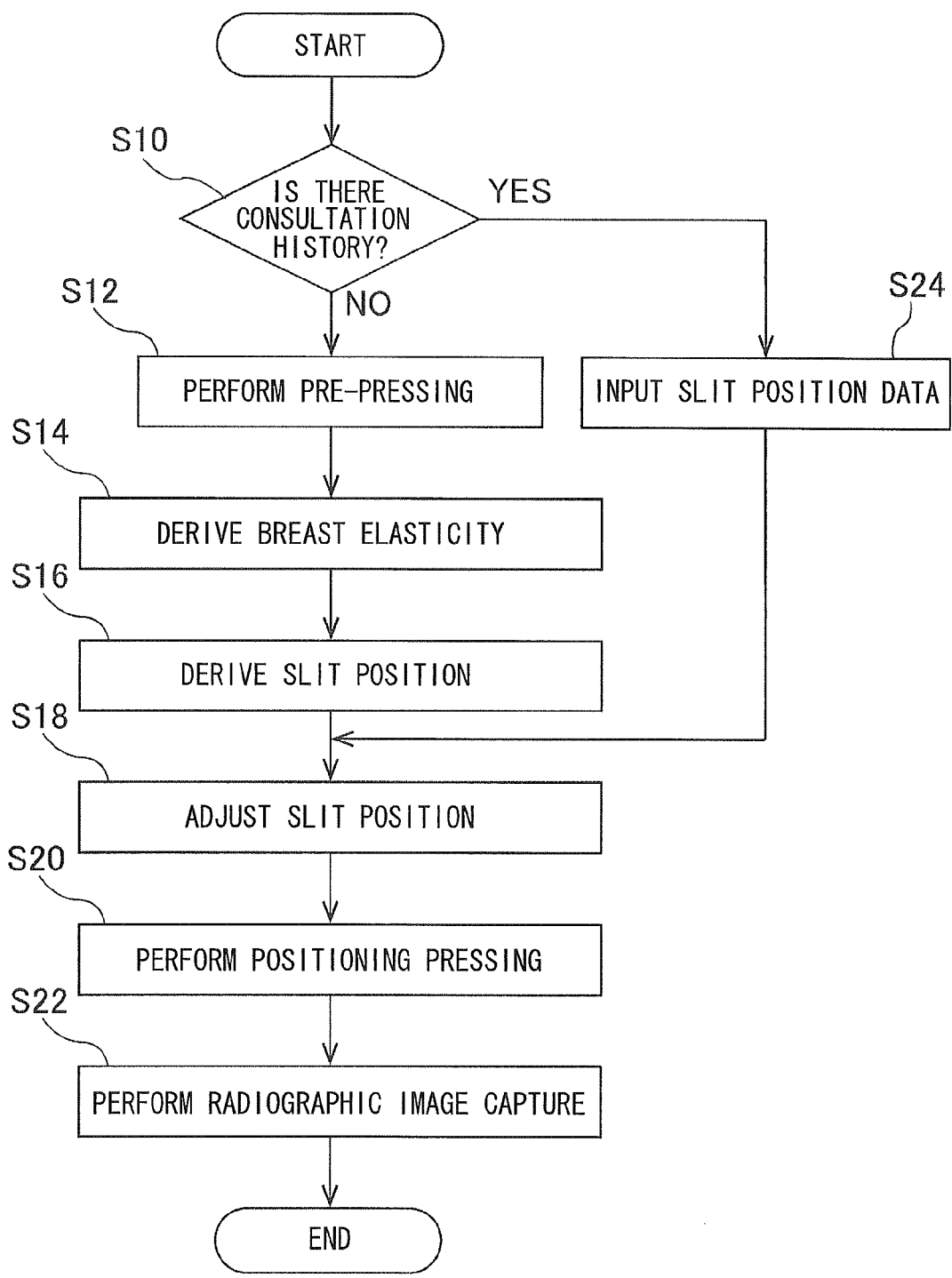
FIG. 9 is a control flow chart of a radiographic imaging apparatus illustrated in FIG. 1.

Operation of the radiographic imaging apparatus 10 and the press plate 26 according to the first exemplary embodiment is as follows. As illustrated in FIG. 9, the first determination is made as to whether or not there is any consultation history for the examinee W (S10). Having a consultation history means that a radiographic image of the breast N has been captured in the past, and that there exists data available for determining a deformation amount of the press section 26A of the press plate 26 during the image capture. It follows that not having any consultation history means that no such data exists. Determination as to whether or not there is consultation history is executed by the radiographic imaging apparatus 10. Namely, when the data necessary to determine whether or not there exists past consultation history is input from the operation panel 46 illustrated in FIG. 4, the imaging apparatus controller 48 searches past consultation histories stored in the storage section 47. The data necessary to determine refers here to at least one item of, for example, the name, the health insurance number or the patient registration card number of the examinee W. As a result of the search, when there is stored corresponding data in the storage section 47, the imaging apparatus controller 48 determines that there exists consultation history. On the other hand, the imaging apparatus controller 48 determines that there is no consultation history when there is no corresponding data stored in the storage section 47. Note that the determination as to whether or not there is consultation history may be performed also by the interview with the examinee W by a doctor. In such cases, based on the determination result, the doctor or the operator of the radiographic imaging apparatus 10 inputs the determination result through the operation panel 46.

In cases in which there is no consultation history for the examinee W, the pre-pressing of the breast N of the examinee W is performed in the radiographic imaging apparatus 10

(S12). The pre-pressing is pressing performed prior to the positioning pressing during the main radiographic image capture. Specifically, in the pre-pressing the breast N is interposed between the imaging face 20 of the imaging table 22 and the press section 26A of the press plate 26, the breast N is pressed with a light pressing force that does not cause pain to the examinee W, with a pressing force of for example about 60N to 80N.

Figure 10A:
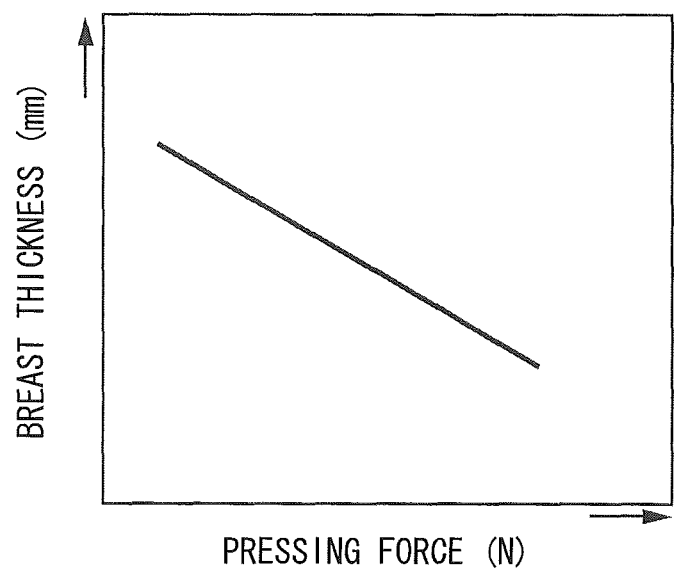
FIG. 10A is a graph illustrating a relationship between the pressing force and breast thickness to adjust the deformation amount of a press section of a press plate in the radiographic imaging apparatus illustrated in FIG. 9.

An example of a relationship between pressing force and thickness of the breast N is illustrated in FIG. 10A. In FIG. 10A, the horizontal axis is pressing force (N) and the vertical axis is the breast N thickness (mm). As illustrated in FIG. 10A, generally the thickness of the breast N tends to become thinner as the pressing force is increased, however there is some difference in this trend due to differences among breasts N of examinees W, one of which is, for example, mammary gland density. In pre-pressing, the thickness of the breast N is measured when the pressing force is applied, and the breast elasticity (N/mm) is derived from the relationship between the applied pressing force and the measured thickness (S14). The breast elasticity is the value which is derived by dividing the pressing force by the thickness. Derivation of the breast elasticity is performed by employing a table that can derive a value for the breast elasticity from the relationships between the values of pressing force and values of thickness of breast N. Such a table is pre-stored in the storage section 47 of the radiographic imaging apparatus 10, as referred to above and illustrated in FIG. 4. Since these values of breast elasticity do not need to be of extremely high precision, it is advantageous for these values to be treated as digital values with a certain width. Namely, the breast elasticity is derived using the table, and as a result it is possible to make the size (for example the computation power) of the system for this derivation smaller by using certain width ranges. Moreover, in the imaging apparatus controller 48 illustrated in FIG. 4, configuration may be made such that the program 53 contains a computation formula is pre-stored in the ROM 52, and that the breast elasticity is derived by computation with the CPU 51 on input of the value of the pressing force and the value of the thickness of the breast N through the operation panel 46. Moreover, in the radiographic imaging apparatus 10 illustrated in FIG. 4, a dedicated circuit may be configured to derive breast elasticity. Note that the value of breast elasticity may be derived by fixing one of the pressing force or the thickness of the breast N, and deriving the other value using for example a table.

Figure 10B:
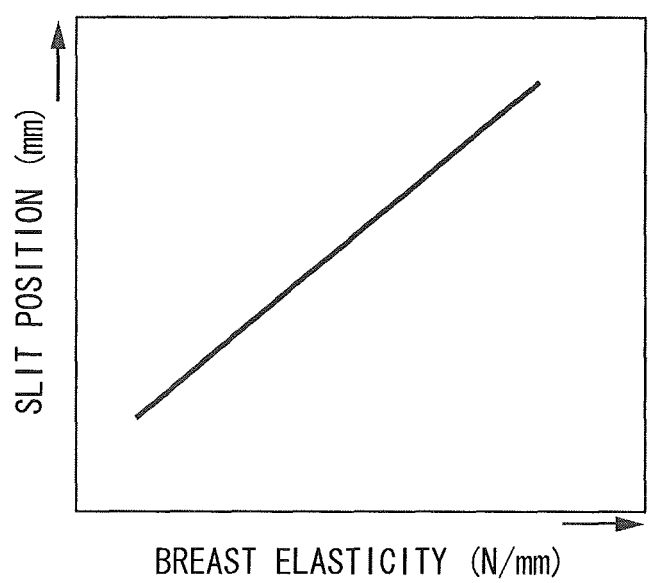
FIG. 10B is a graph illustrating a relationship between breast elasticity and slit position.

When the breast elasticity has been derived, the position of the movable support point portions 262 in the slits 26E of the press plate 26 is derived, as illustrated in FIG. 10B (S16). In FIG. 10B, the horizontal axis is the breast elasticity (N/mm). The vertical axis is the position (mm) of the movable support point portions 262 in the slits 26E, and in this case is the position of the movable support point portions 262 in the slits 26E from the front face side of the press plate 26 to as far as the rear face side. The value of the breast elasticity is higher when the breast N of the examinee W is harder, with the examinee W generally relatively more susceptible to feeling pain. Thus the deformation amount on the front face side of the press section 26A is adjusted to be large by positioning the movable support point portions 262 in the slits 26E at the rear face side of the press plate 26 or in the vicinity thereof. On the other hand, the value of breast elasticity is lower when the breast N of the examinee W is softer, and the examinee W is generally relatively less susceptible to feeling pain. Thus the deformation amount on the front face side of the press section 26A is adjusted to be small by positioning the movable support point portions 262 in the slits 26E at the front face side of the press plate 26 or the vicinity thereof. For a similar reason to those when deriving the breast elasticity, to derive the position of the movable support point portions 262, a table to derive the position of the movable support point portions 262 from the values of the breast elasticity is also employed. Such a table is pre-stored in the storage section 47 of the radiographic imaging apparatus 10, illustrated in FIG. 4. Configuration may also be made such that derivation of the position of the movable support point portions 262 is derived by computation or by using a dedicated circuit, similarly to when driving the breast elasticity.

Next, based on the derived position, the movable support point portions 262 is moved in the slits 26E of the press plate 26, and adjustment of this position is performed (S18). In such adjustment of this position, the data of the position of the movable support point portions 262 in the slits 26E is read into the imaging apparatus controller 48 from the table stored in the storage section 47 of the radiographic imaging apparatus 10 illustrated in FIG. 4. In the imaging apparatus controller 48, the drive force of the drive source 264 is controlled based on this position data. The drive force of the drive source 264 is transmitted to the transmission mechanism 268 illustrated in FIG. 5, FIG. 6 and FIG. 8. In the transmission mechanism 268, the drive force of the drive source 264 is transmitted respectively to the gear wheel 268A, the gear wheel 268B, the rotation transmission shaft 268C, the drive side bevel gears 268D, the following side bevel gears 268E and the rotation transmission shafts 268F. When the drive force is transmitted to the rotation transmission shafts 268F, the movable portions 268G move along the axial direction of the male threaded drive sections 268FS due to meshing of the male threaded drive sections 268FS of the rotation transmission shafts 268F and the female drive threaded drive sections of the movable portions 268G. The movable portions 268G are coupled to the movable support point portions 262, and so ultimately the movable support point portions 262 are moved to the derived position along the extension direction of the slits 26E. The adjustment of the movement position is performed by adjustment of the drive amount of the drive source 264, such as for example by adjusting the number of times rotation in the case of an electric motor. Moreover, fine adjustment of the movement position may be performed by adjusting the drive amount of the drive source 264 based on the detection result of movement position of the movable support point portions 262 obtained by the pivot point position sensor 45 illustrated in FIG. 4. Adjustment of the deformation amount of the press section 26A of the press plate 26 is completed by adjusting the movement position of the movable support point portions 262 in the slits 26E. Note that configuration may be made such that adjustment is made to the movement position whilst monitoring the detection result of the pivot point position sensor 45.

The manual adjustment section 269 is operated by an operator in cases in which adjustment of the movement position is not made automatically, or in cases in which fine adjustment of the movement position is performed manually. The coupling of the drive source 264 to the gear wheel 268A of the transmission mechanism 268 is released by the clutch 266 when the manual adjustment section 269 is being operated.

When at step S10 there is consultation history of the examinee W, the past data for determining the deformation amount of the press section 26A of the press plate 26 is stored in the storage section 47 illustrated in FIG. 4, and so this data is input to the imaging apparatus controller 48 from the storage section 47 (S24). Then at step S18, based on the input data similar adjustment is performed to the position of the movable support point portions 262. Note that data for determining the deformation amount may also be input by a doctor or operator through the operation panel 46.

Next, positioning pressing is executed on the breast N of the examinee W by the press plate 26 with adjusted deformation amount of press section 26A (S20). The positioning pressing is pressing executed during actual radiographic imaging, and for example presses the breast N with a pressing force of for example about 80N to 120N. A portion of the press section 26A is formed with a local face profile so as to project out towards the imaging face 20 side, thereby enabling the breast N to be pressed evenly overall by the positioning pressing. The deformation amount of the press section 26A of the press plate 26 is adjusted to optimize according to the hardness of the breast N. The examinee W is accordingly less susceptible to feeling pain even though the breast N is being pressed.

In the state of positioning pressing, bremsstrahlung radiation is then irradiated from the radiation irradiation section 24 illustrated in FIG. 1 towards the breast N, and a radiographic image of the breast N is captured through the radiation detector 42 of the imaging table 22 (S22). Then, the breast N pressed by the press plate 26 is released, thereby completing the image capture.

Operation and Advantageous Effects of the First Exemplary Embodiment

In the press plate 26 according to the first exemplary embodiment, the movable support point portions 262 are capable of moving between the press section 26A and the support section 26B. Namely, the position of support of the movable support point portions 262 with respect to the press section 26A changes. A change occurs in the support structure for the support section 26B to support the press section 26A through the movable support point portions 262 according to the movement position of the movable support point portions 262 (see at (B) to (D) in FIG. 7). By changing the support structure, there is a change in the reaction force received from the image capture body by the press section 26A, enabling the profile of the press section 26A to be changed, and enabling the deformation amount of the press section 26A to be adjusted. An optimal deformation amount of the press section 26A can accordingly be achieved for the pressed state with the same pressing force. The press plate 26 attached to the mammography equipment as the radiographic imaging apparatus 10 is accordingly able to adjust the deformation amount of the press section 26A according to the examinee W, even when the breast N of the examinee W is squashed between the imaging face 20 of the imaging table 22 and the press section 26A in the pressed state with the same pressing force. The pain caused to an examinee W can accordingly be reduced by making the deformation amount of the press section 26A larger for an examinee W who is susceptible to feeling pain.

Moreover, in the press plate 26 according to the first exemplary embodiment, configuration is made with the press section 26A and the support section 26B integrally provided, and with the slits 26E provided as the separation portions between the press section 26A and the support section 26B. Thus a simple structure of the press plate 26 can be implemented since the press section 26A and the support section 26B are obtained by configuring from the same member (a single material) with the separation portions configured by the slits 26E. Moreover, due to being provided with a simple structure, the press plate 26 can also be easily produced (manufactured). A reduction in manufacturing cost of the press plate 26 can accordingly be achieved.

Moreover, in the press plate 26 according to the first exemplary embodiment, the movable support point portions 262 are capable of moving along the extension directions of the slits 26E. The deformation amount of the press section 26A can accordingly be adjusted according to the distance from the moved position of the movable support point portions 262 from one end portion side of the press section 26A, for example from the front face side.

Moreover, the press plate 26 according to the first exemplary embodiment is provided with the slits 26E on the side faces, and so the deformation amount of the press section 26A is adjustable in the front-rear direction as viewed from the examinee W. Since there is more susceptibility to feeling pain when pressure is applied to the base of the breast N of the examinee W, the pain caused to the examinee W can be reduced by making the deformation amount larger at the press section 26A at locations corresponding to the breast N base position.

Moreover, in the press plate 26 according to the first exemplary embodiment, the breast N is sandwiched between the imaging face 20 and the press section 26A, is softer than the press section 26A, and has a local surface profile that projects out towards the press section 26A side. The central portion of the breast N is pressed by the local surface profile of the press section 26A, and the periphery thereof is pressed out. The thickness of the breast N sandwiched between the imaging face 20 and the press section 26A can accordingly be made uniform, enabling the precision of radiographic image capture to be improved. Moreover, the radiation amount to capture the radiographic image can also be reduced.

Moreover, the press plate 26 according to the first exemplary embodiment is equipped with the drive source 264 and the transmission mechanism 268 that transmits drive force of the drive source 264 to the movable support point portions 262, thereby enabling automation of the movement and positioning of the movable support point portions 262 in the slits 26E.

In the press plate 26 according to the first exemplary embodiment, the manual adjustment section 269 is provided coupled to the transmission mechanism 268, thereby enabling the movement and positioning of the movable support point portions 262 to be performed manually using the manual adjustment section 269 separately to the drive force from the drive source 264.

Moreover, the radiographic imaging apparatus 10 according to the first exemplary embodiment is equipped with the press plate 26, the imaging table 22, the radiation irradiation section 24, and the imaging apparatus controller 48. The imaging apparatus controller 48 is configured to control drive force of the drive source 264 and to adjust the movement and positioning of the movable support point portions 262 through the transmission mechanism 268. The movement and positioning of the movable support point portions 262 of the press plate 26 can accordingly be performed automatically by the imaging apparatus controller 48, thereby enabling automatic adjustment to be made of the deformation amount of the press section 26A of the press plate 26.

Moreover, in the radiographic imaging apparatus 10 according to the first exemplary embodiment, the movement and positioning of the movable support point portions 262 is adjusted by the imaging apparatus controller 48 based on at least one type of data selected from the group consisting of the pressed thickness of the breast N of the examinee W and the pressing force. The deformation amount of the press section 26A of the press plate 26 can accordingly be adjusted according to the examinee W.

Second Exemplary Embodiment

Explanation follows regarding an example in which the adjustment of the deformation amount of the press section 26A of the press plate 26 in a radiographic imaging apparatus 10 according to the first exemplary embodiment is implemented in a second exemplary embodiment of the present invention based on human tissue of an image capture body.

Operation of Radiographic Imaging Apparatus and Press Plate

Figure 11:
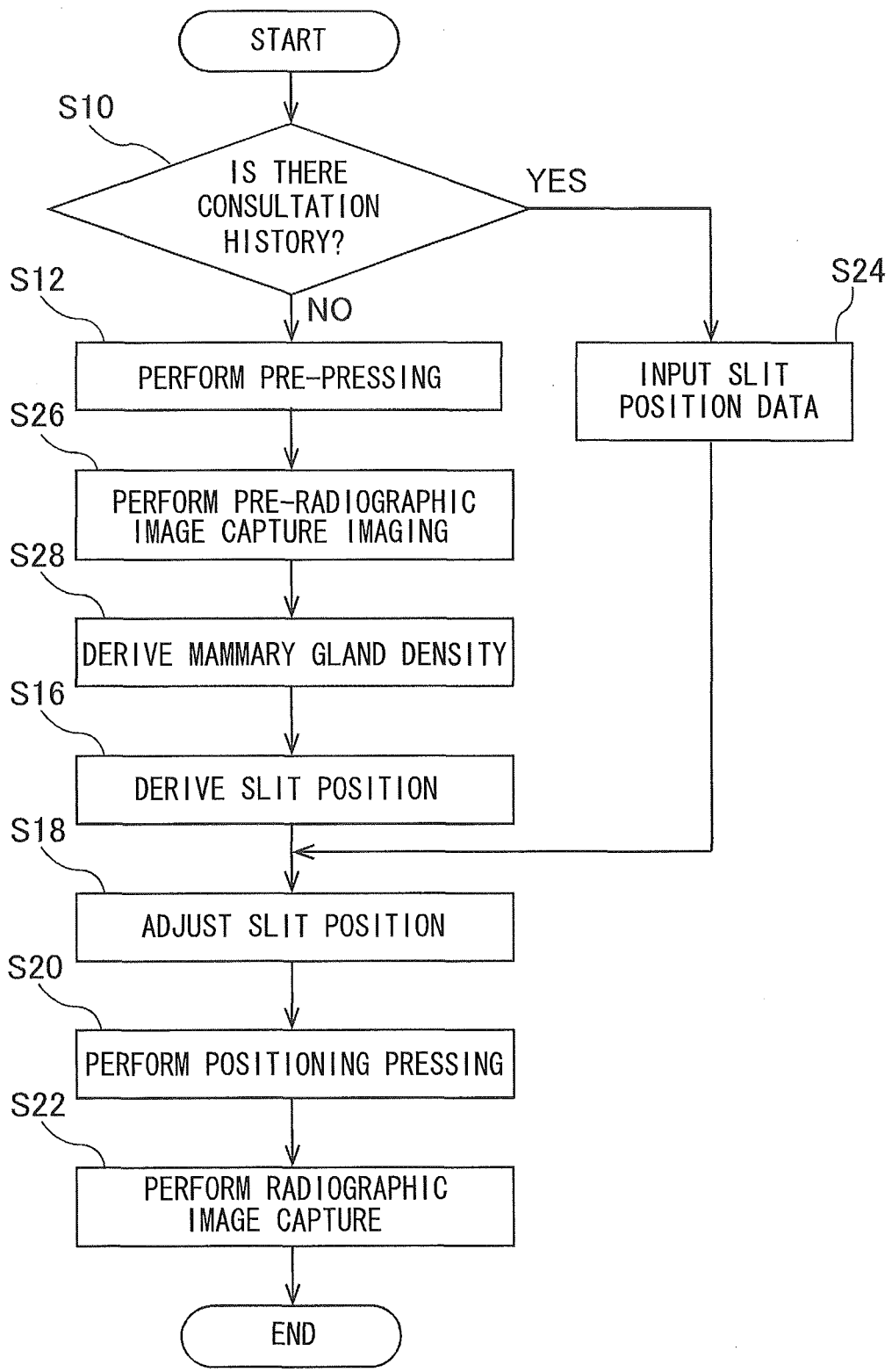
FIG. 11 is a control flow chart of a radiographic imaging apparatus according to a second exemplary embodiment of the present invention.

Operation of a radiographic imaging apparatus 10 and a press plate 26 according to the second exemplary embodiment is as follows. As illustrated in FIG. 11, similarly to the operation of the radiographic imaging apparatus 10 and the press plate 26 in the first exemplary embodiment, the pre-pressing of step S12 is executed in cases in which there is no consultation history as a result of determination of consultation history at step S10.

After pre-pressing, pre-radiographic image capture is executed (S26). The pre-radiographic image capture is radiographic imaging performed with the amount of radiation that enables at least the density of human tissue of the breast N of the examinee W, in this case the mammary gland density, to be measured. Thus the amount of radiation for the pre-radiographic image capture is set lower than the radiation amount for the actual radiographic image capture at step S22. For example, the radiation amount may be set at 0.2mGy for the pre-radiographic image capture and it is set at 2mGy for the radiographic image capture.

Figure 12A:
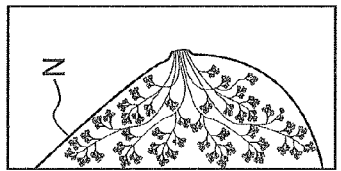
FIG. 12A, FIG. 12B, FIG. 12C, FIG. 12D, FIG. 12E and FIG. 12F are outline diagrams that schematically illustrate imaged images of a breast as viewed from the side for adjusting the deformation amount of a press section of a press plate in a radiographic imaging apparatus according to a second exemplary embodiment.
Figure 12B:
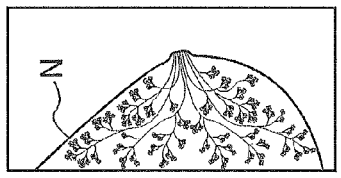
Figure 12C:
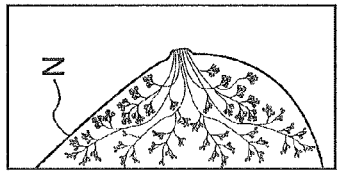
Figure 12D:
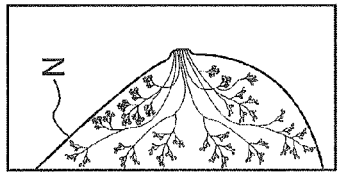
Figure 12E:
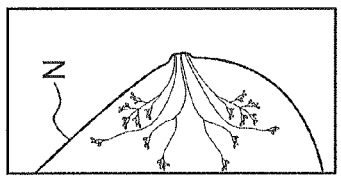
Figure 12F:
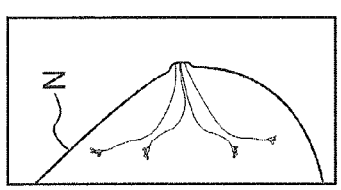

The mammary gland density of the breast N is derived based on a radiographic image obtained by the pre-radiographic image capture (S28). The image of the breast N captured by irradiation of X-rays from the side of the examinee W is schematically illustrated in 6 samples from FIG. 12A to FIG. 12F. The locations of mammary glands are illustrated inside the breast N. The proportion of mammary gland per unit volume (per unit of cross-sectional area in the illustration) increases on progression from sample in FIG. 12A to the sample in FIG. 12F. In the images of X-ray image capture, the mammary gland density can be computed from a ratio of the area of the mammary gland to the breast N cross-sectional area. For example, there is a tendency for the mammary gland density (%) to increase on progression from the sample illustrated in FIG. 12A towards the sample illustrated in FIG. 12F. With reference to the mammary gland density of the breast N in the sample illustrated in FIG. 12A, the mammary gland density of the sample illustrated in FIG. 12B is 5% to 10% higher than that of the sample in FIG. 12A, the mammary gland density of the sample illustrated in FIG. 12C is 15% to 20% higher than that of the sample in FIG. 12A, the mammary gland density of the sample illustrated in FIG. 12D is 25% to 40% higher than that of the sample in FIG. 12A, mammary gland density of the sample illustrated in FIG. 12E is 50% to 70% higher than that of the sample in FIG. 12A, and the mammary gland density of the sample illustrated in sample in FIG. 12F is 75% to 80% higher than that of the sample in FIG. 12A.

Figure 12G:
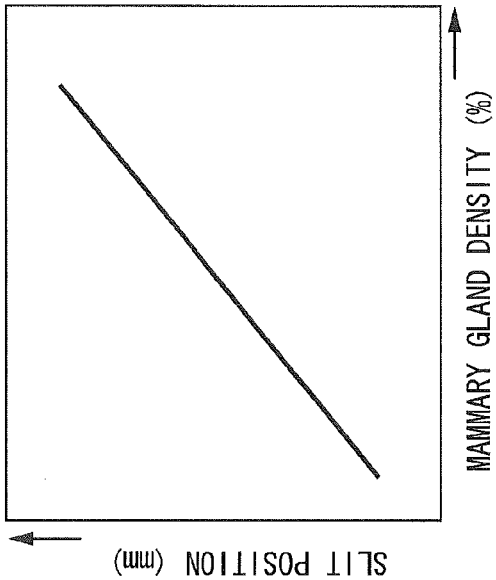
FIG. 12G is a graph illustrating a relationship between mammary gland density and slit position.

When the mammary gland density of the breast N has been derived, the position of the movable support point portions 262 in the slits 26E of the press plate 26 is derived, as illustrated in FIG. 12G (S16). In FIG. 12G, the horizontal axis is mammary gland density (%), and, similarly to the vertical axis illustrated in FIG. 10B, the vertical axis is the position (mm) of the movable support point portions 262 in the slits 26E. The breast N is harder when the mammary gland density of the breast N of the examinee W is high, and generally the examinee W is relatively susceptible to feeling pain. The movable support point portions 262 are accordingly adjusted in the slits 26E so as to be positioned at the rear face side of the press plate 26, or at positions in the vicinity thereof, such that the deformation amount of the front face side of the press section 26A is large. On the other hand, the breast N is softer when the mammary gland density of the breast N of the examinee W is low, and generally the examinee W is relatively less susceptible to feeling pain. The movable support point portions 262 are accordingly adjusted in the slits 26E so as to be positioned at the front face side of the press plate 26, or at positions in the vicinity thereof, such that the deformation amount of the front face side of the press section 26A is small. For a similar reason to those when deriving the breast elasticity according to the first exemplary embodiment, to derive positions of the movable support point portions 262, a table to derive the positions of the movable support point portions 262 from values of the mammary gland density is also employed. Such a table is pre-stored in the storage section 47 of the radiographic imaging apparatus 10 illustrated in FIG. 4. Note that derivation of the position of the movable support point portions 262 may also be derived by computation or derived using a dedicated circuit.

Next, based on the derived position, the movable support point portions 262 are moved in the slits 26E of the press plate 26, and its positioning is performed (S18). The adjustment method of the position of the movable support point portions 262 is similar to the adjustment method of the position of the movable support point portions 262 according to the first exemplary embodiment. Note that when there is consultation history of the examinee W at step S10, the necessary data is input at step S24. Then at step S18, adjustment is performed of the position of the movable support point portions 262 based on the input data.

Positioning pressing of the breast N of the examinee W is then executed by the press plate 26 with adjusted deformation amount of the press section 26A (S20). In the positioning pressing, the deformation amount of the press section 26A of the press plate 26 is adjusted to optimize according to the mammary gland density of the breast N. The examinee W is accordingly not susceptible to feeling pain even though the breast N is pressed.

In the state of positioning pressing, bremsstrahlung radiation is irradiated from the radiation irradiation section 24 illustrated in FIG. 1 towards the breast N, and a radiographic image of the breast N is captured using the radiation detector 42 of the imaging table 22 (S22). Then, the breast N pressed by the press plate 26 is released, thereby completing the image capture.

Operation and Advantageous Effects of Second Exemplary Embodiment

In the press plate 26 and the radiographic imaging apparatus 10 according to the second exemplary embodiment, operation and advantageous effects can be obtained, which are similar to those obtained from the press plate 26 and the radiographic imaging apparatus 10 of the first exemplary embodiment.

Moreover, in the radiographic imaging apparatus 10 according to the second exemplary embodiment, the adjustment of the support force of the reaction force section 26C is controlled by the imaging apparatus controller 48 based on the density of human tissue, or more specifically, on the density of the mammary gland density data. Thus the deformation amount of the press section 26A of the press plate 26 can be automatically adjusted according to the breast N of the examinee W.

Note that although in the second exemplary embodiment the mammary gland density is employed as the density of human tissue, there is no limitation thereto. For example, tissue such as subcutaneous fat or Cooper's ligament may be employed as human tissue. Moreover, with respect to derivation of the density of human tissue there is also no limitation to using radiographic image capture, and combined use of ultrasound detection is possible.

Third Exemplary Embodiment

Explanation follows regarding a third exemplary embodiment of the present invention, this being an example in which the adjustment of deformation amount of the press section 26A of the press plate 26 in the radiographic imaging apparatus 10 according to the second exemplary embodiment is executed based on a radiation transmissivity of an image capture body.

Overall Configuration of Radiographic Imaging Apparatus

Figure 13:
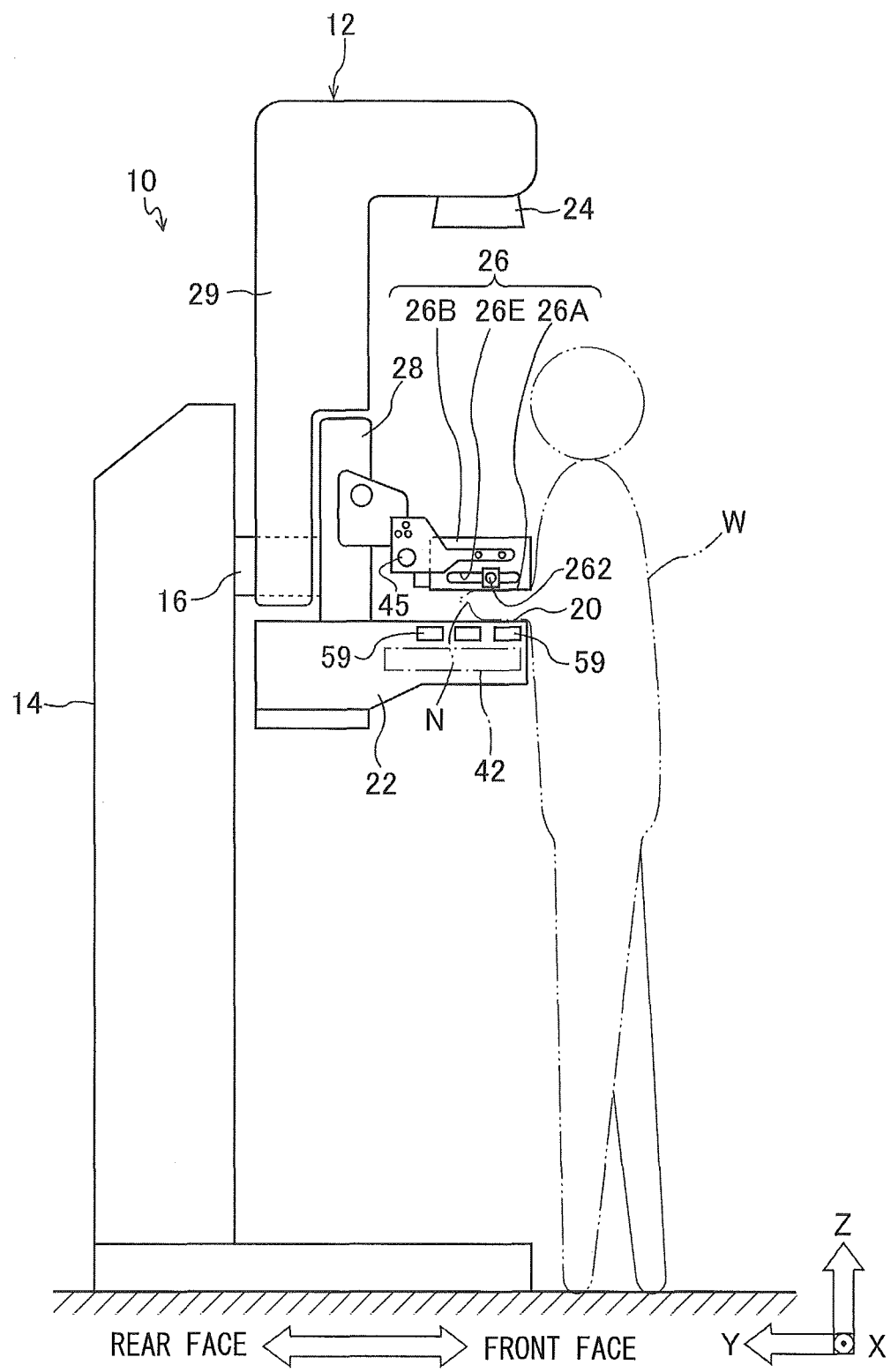
FIG. 13 is a schematic side view for explaining an overall configuration of a radiographic imaging apparatus according to a third exemplary embodiment of the present invention.
Figure 14:
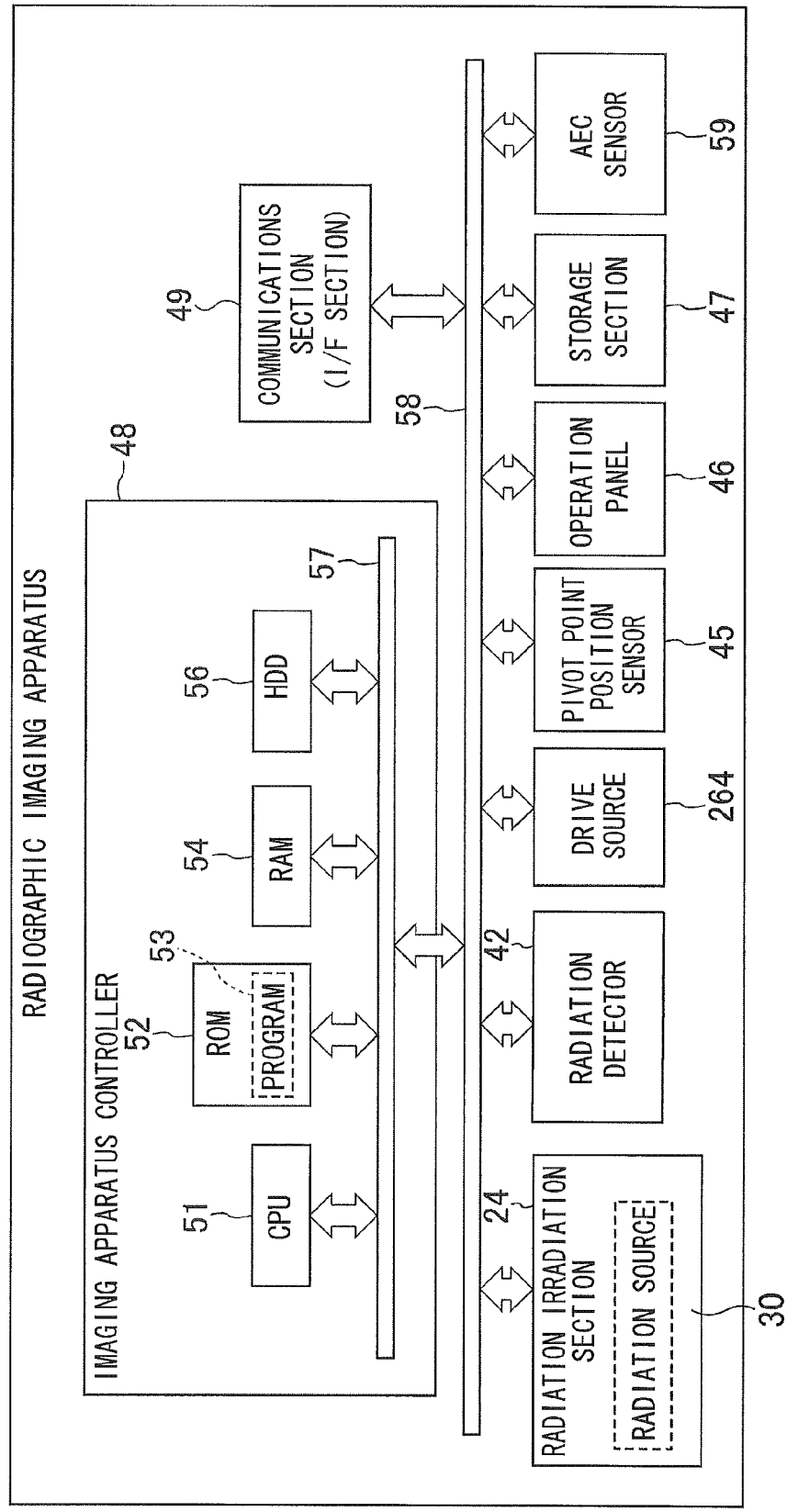
FIG. 14 is an overall system block diagram of the radiographic imaging apparatus illustrated in FIG. 13.

As illustrated in FIG. 13, a radiographic imaging apparatus 10 according to a third exemplary embodiment is provided with Automatic Exposure Controller (AEC) sensors 59, which are built inside an imaging table 22 and between an imaging face 20 and a radiation detector 42. Plurality of the individual AEC sensors 59 are disposed in a matrix shape in plan view of the imaging face 20, although not illustrated in the drawings. For example, there are 9 individual AEC sensors 59 disposed 3 by 3 across in the X direction and across in the Y direction. As illustrated in FIG. 14, the AEC sensors 59 are connected to the imaging apparatus controller 48 and other sections through the common bus 58.

Operation and Advantageous Effects of Radiographic Imaging Apparatus

At step S26 of a control flow chart illustrated in FIG. 11 for the radiographic imaging apparatus 10 according to the second exemplary embodiment, the AEC sensors 59 are irradiated in the pre-radiographic image capture, and the radiation amount that has passed through the breast N of the examinee W is measured. Moreover, the thickness of the breast N is measured at the time the radiation amount is measured. The radiation transmissivity of the breast N can be derived based on the result of measuring the radiation amount and the thickness of the breast N. This radiation transmissivity can be easily derived in the imaging apparatus controller 48 from the measurement result of the radiation amount transmitted from the AEC sensors 59, and from the thickness of the breast N input through the operation panel 46. Similarly to in the radiographic imaging apparatus 10 according to the first exemplary embodiment, any method out of a table, computation or a dedicated circuit are employable as the derivation method.

When the radiation transmissivity of the breast N is derived, the position of the movable support point portions 262 in the slits 26E of the press plate 26 can be derived based on the radiation transmissivity. For example, in cases in which the radiation transmissivity of the breast N of the examinee W is low due to a high mammary gland density, the breast N is hard, and generally the examinee W is relatively more susceptible to feeling pain. The movable support point portions 262 are accordingly adjusted in the slits 26E so as to be positioned at the rear face side of the press plate 26, or at a position in the vicinity thereof, such that the deformation amount of the front face side of the press section 26A is large. However, in cases in which the radiation transmissivity of the breast N of the examinee W is high due to a low mammary gland density, the breast N is softer, and generally the examinee W is relatively less susceptible to feeling pain. The movable support point portions 262 are accordingly adjusted in the slits 26E so as to be positioned at the front face side of the press plate 26, or at a position in the vicinity thereof, such that the deformation amount of the front face side of the press section 26A is small. For a similar reason to those when deriving the breast elasticity according to the first exemplary embodiment, to derive the position of the movable support point portions 262, a table to derive the positions of the movable support point portions 262 from values of the radiation transmissivity and thickness of the breast N is also employed. Such a table is pre-stored in the storage section 47 of the radiographic imaging apparatus 10 illustrated in FIG. 4. Note that derivation of the position of the movable support point portions 262 may also be derived by computation or derived using a dedicated circuit.

Processing from step S18 afterwards of the control flow chart illustrated in FIG. 11 is then executed, and a radiographic image of the breast N is captured.

Operation and Advantageous Effects of the Third Exemplary Embodiment

According to the press plate 26 and the radiographic imaging apparatus 10 according to the third exemplary embodiment, similar operation and advantageous effects may be obtained to those obtained by the press plate 26 and the radiographic imaging apparatus 10 according to the second exemplary embodiment.

Moreover, in the radiographic imaging apparatus 10 according to the third exemplary embodiment, the movement and positioning of the movable support point portions 262 is controlled by the imaging apparatus controller 48 based on the radiation transmissivity data. The deformation amount of the press section 26A of the press plate 26 can accordingly be adjusted automatically according to the breast N of the examinee W.

Fourth Exemplary Embodiment

A fourth exemplary embodiment of the present invention will be explained by an example in which the examinee W is prevented from being trapped in the slits 26E of the press plate 26 according to any of the first to the third exemplary embodiments.

Press Plate Configuration

Figure 15A:
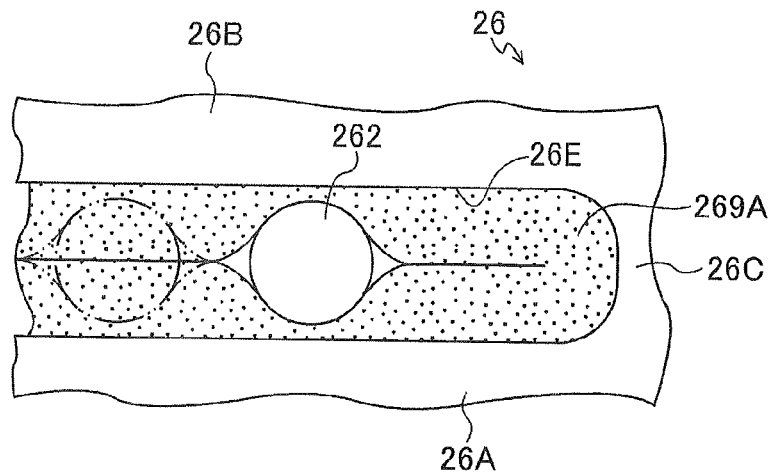
FIG. 15A is an enlarged side view of relevant portions of a press plate of a radiographic imaging apparatus according to a fourth exemplary embodiment of the present invention.

In a press plate 26 according to the fourth exemplary embodiment, as illustrated in FIG. 15A, a trapping prevention component 269A is provided at the periphery of movable support point portions 262 of the slits 26E to close off the slits 26E. A cut is provided in the trapping prevention component 269A right at the intermediate portion between the press section 26A and the support section 26B and running along the extension direction of the slits 26E. The cut enables movement of the movable support point portions 262 in the slits 26E, and is configured to close off the periphery of the position of the movable support point portions 262 even with movement.

The trapping prevention component 269A is configured from a soft material that has excellent shape-rebound properties, and has more resilience than the material of the press plate 26, such as a rubber or a sponge. This soft material is bonded to the inside walls of the slits 26E, for example by an adhesive.

Operation and Advantageous Effects of the Fourth Exemplary Embodiment

In the press plate 26 according to the fourth exemplary embodiment, the openings of the slits 26E are closed off by the trapping prevention component 269A, and so the examinee W can be prevented from getting for example a chest wall region trapped in the openings of the slits 26E.

Configuration of a Press Plate of A First Modified Example

Figure 15B:
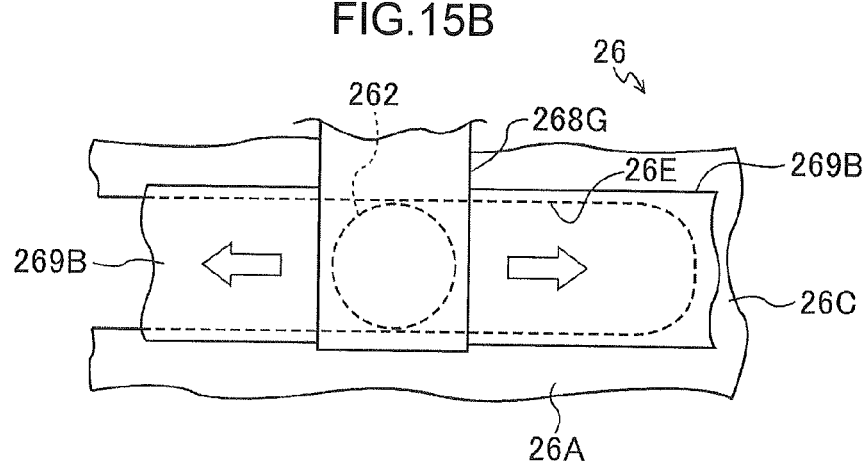
FIG. 15B is an enlarged side view of relevant portions of a press plate according to a first modified example.

A press plate 26 according to a first modified example of the fourth exemplary embodiment is, as illustrated in FIG. 15B, equipped with a trapping prevention component 269B provided at the periphery of the movable support point portions 262 of the slits 26E to close off the slits 26E. The trapping prevention component 269B is coupled to the movable support point portions 262 and is configured as shutters attached to both end portions in the movement direction of movable portions 268G configuring the transmission mechanism 268. The trapping prevention component 269B moves accompanying movement of the movable portions 268G, and is configured to always close off regions other than the movable portions 268G of the slits 26E.

The trapping prevention component 269B is configured from a belt shaped soft material such as cloth or a flexible resin such as polyvinyl or the like.

The press plate 26 according to the first modified example closes off the openings of the slits 26E with the trapping prevention component 269B, and so the examinee W can be prevented from getting for example a chest wall region trapped in the openings of the slits 26E.

Figure 15C:
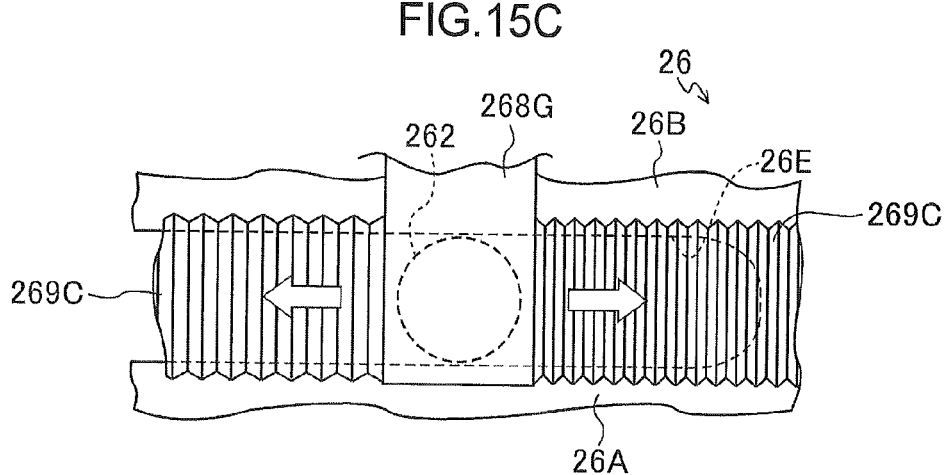
FIG. 15C is an enlarged side view of relevant portions of a press plate according to a second modified example.

A press plate 26 according to a second modified example of the fourth exemplary embodiment is, as illustrated in FIG. 15C, equipped with a trapping prevention component 269C provided at the periphery of the movable support point portions 262 of the slits 26E to close off the slits 26E. The trapping prevention component 269C is coupled to the movable support point portions 262 and is configured in a concertina attached to both end portions in the movement direction of movable portions 268G configuring the transmission mechanism 268. The trapping prevention component 269C expands and contracts accompanying movement of the movable portions 268G, and is configured to always close off regions other than the movable portions 268G of the slits 26E.

The trapping prevention component 269C is configured from as a concertina shaped soft material such as cloth or a flexible resin such as polyvinyl or the like.

Operation And Advantageous Effects of The Second Modified Example

The press plate 26 according to the second modified example closes off the openings of the slits 26E with the trapping prevention components 269C, and so the examinee W can be prevented from getting for example a chest wall region trapped in the openings of the slits 26E.

Fifth Exemplary Embodiment

A fifth exemplary embodiment of the present invention will be explained by an example in which the deformation amount at the front face side (the examinee W side) of the press section 26A is adjustable in the press plate 26 according to any of the first to the fourth exemplary embodiments.

Configuration of Press Plate

Figure 16:
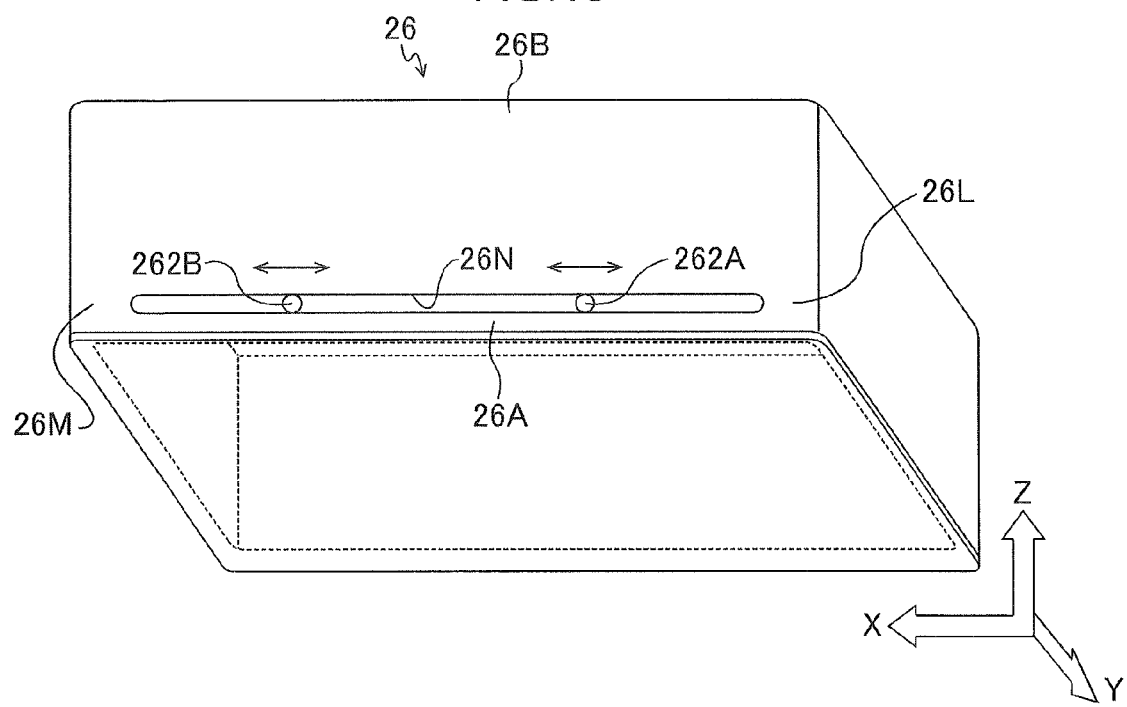
FIG. 16 is a perspective view from the front face side of a press plate of a radiographic imaging apparatus according to a fifth exemplary embodiment of the present invention.

As illustrated in FIG. 16, a press plate 26 according to the fifth exemplary embodiment includes at least a press section 26A, a support section 26B, and plural movable support point portions 262A and 262B. The respective basic configurations of the press section 26A and the support section 26B are respectively configured similarly to the press section 26A and the support section 26B of the press plate 26 according to the first exemplary embodiment. The movable support point portions 262A and 262B are provided at a separation portion between the press section 26A and the support section 26B at the front face of the press plate 26 that is on the examinee W side. The movable support point portions 262A and 262B are movable in the X direction between the press section 26A and the support section 26B. The movement direction of the movable support point portion 262B is the opposite direction to the movement direction of the movable support point portion 262A. Namely, as viewed by the examinee W, the movable support point portion 262B moves to the left hand side when the movable support point portion 262A moves to the right hand side, and the movable support point portion 262B moves to the right hand side when the movable support point portion 262A moves to the left hand side. The deformation amount at the front face side of the press section 26A is accordingly adjustable by moving the movable support point portions 262A and 262B.

Namely, the press plate 26 is configured with the press section 26A and the support section 26B that are separated from each other by a slit 26N that is provided extending from one end portion side to another end portion side on the front face of the press section 26A and the support section 26B, and with both end portions of the press section 26A and the support section 26B coupled together. One end side of the press section 26A and one end side of the support section 26B are accordingly coupled together by a coupling portion 26L, and the other end side of the press section 26A and the other end side of the support section 26B are accordingly coupled together by a coupling portion 26M.

Although omitted from illustration in the drawings, the movable support point portions 262A and 262B are configured equipped with configuration of the drive source 264, the transmission mechanism 268, the manual adjustment section 269 and the imaging apparatus controller 48 etc. according to the first exemplary embodiment. Consequently, it is possible to automatically or manually perform movement and positioning of the movable support point portions 262A and 262B in the slit 26N. Note that since it is possible that the chest wall of the examinee W makes contact with the front face of the press plate 26 at least part of particularly the transmission mechanism 268 is provided internally to the press plate 26.

Operation of Radiographic Imaging Apparatus and Press Plate

The operation of the radiographic imaging apparatus 10 and the press plate 26 according to the fifth exemplary embodiment is as follows. In the press plate 26, the movement and positioning of the movable support point portions 262A and 262B in the slit 26N is controlled and implemented according to at least one factor from the list consisting of the breast elasticity as derived according to the first exemplary embodiment, the mammary gland density as derived according to the second exemplary embodiment and the radiation transmissivity as derived according to the third exemplary embodiment.

When the movable support point portions 262A and 262B are both moved towards a central portion in the slit 26N, at the center portion of the press section 26A, the press section 26A is more supported by the support section 26B though the movable support point portions 262A and 262B, and so the deformation amount of the press section 26A is small. This is an optimum adjustment for a soft breast N, an examinee W who is generally not so susceptible to feeling pain. However, at the center portion of the press section 26A, the press section 26A is less supported by the support section 26B through the movable support point portions 262A and 262B when the movable support point portion 262A is moved to one end portion side of the slit 26N and the movable support point portion 262B is moved to the other end portion side of the slit 26N, leading to a large deformation amount of the press section 26A. This is an optimum adjustment for a hard breast N, an examinee W who is generally more susceptible to feeling pain.

Moreover, the movement and positioning of the movable support point portions 262A and 262B in the slit 26N need not be coupled to each other. In such cases, a drive source 264 and a transmission mechanism 268 are separately provided for respective movement and positioning of each of the movable support point portions 262A and 262B. Or, the transmission path is changed after performing the movement and positioning of the movable support point portion 262A using the drive force of the drive source 264, and then the movement and positioning of the movable support point portion 262B is performed. For example, there are sometimes differences in the mammary gland density and at the inside and the outside of the breast N derived in a plan view of mammary gland density according to the second exemplary embodiment, and the hardness sometimes differs. In such cases, the deformation amount of the press section 26A may be adjusted according to the differences in hardness between the inside and the outside of the breast N.

Operation and Advantageous Effects of the Fifth Exemplary Embodiment

In the press plate 26 according to the fifth exemplary embodiment, similarly operation and advantageous effects can be obtained to the operation and advantageous effects obtained by the press plate 26 and the radiographic imaging apparatus 10 according to the first to the third exemplary embodiments. Moreover, in the press plate 26 according to the fifth exemplary embodiment, the movable support point portions 262A and 262B are movable between the press section 26A and the support section 26B. A change therefore occurs in the support structure of the support section 26B supporting the press section 26A through the movable support point portions 262A and 262B according to the movement position of the movable support point portions 262A and 262B. The deformation amount of the press section 26A can be adjusted by such changes in the support structure, thereby enabling an optimum deformation amount of the press section 26A to be achieved for the pressed state with the same pressing force.

Note that, preferably one of the trapping prevention components 269A to 269B of the press plate 26 according to the fourth exemplary embodiment is applied to the press plate 26 according to the fifth exemplary embodiment. In particular, a chest wall region of the examinee W can be prevented from becoming trapped during measurement of the breast when the trapping prevention components 269A to 269C is applied at the chest wall side. Moreover, preferably one of the trapping prevention components 269A to 269C is applied to the press plate 26 according to the sixth exemplary embodiment as described below.

Sixth Exemplary Embodiment

Explanation follows in the sixth exemplary embodiment of the present invention regarding a combination of the first exemplary embodiment and the fifth exemplary embodiment.

Press Plate Configuration

Figure 17:
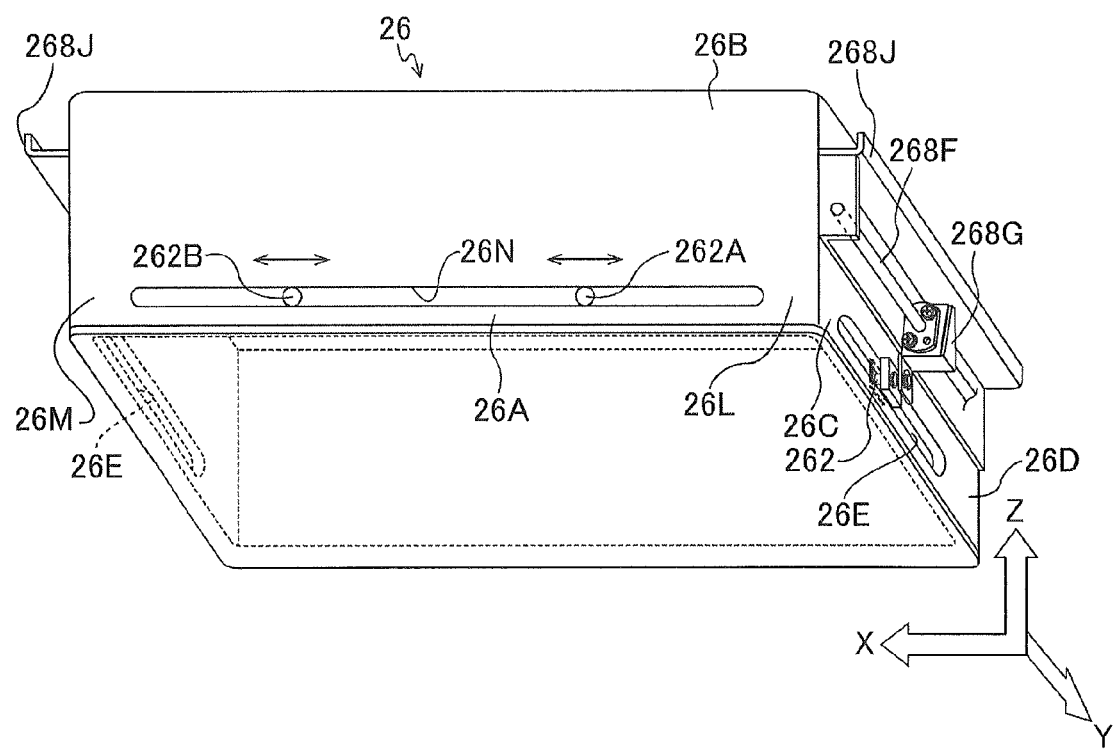
FIG. 17 is a perspective view from the front face side of a press plate of a radiographic imaging apparatus according to a sixth exemplary embodiment of the present invention.

As illustrated in FIG. 17, in the press plate 26 according to a sixth exemplary embodiment, the movable support point portions 262 are movable inside slits 26E provided to side faces, and the movable support point portions 262A and 262B are movable within the slit 26N provided to the front face of the press plate 26. The movement and positioning of the movable support point portions 262 is independently controlled as to the movement and positioning of the movable support point portions 262A and 262B.

Operation and Advantageous Effects of the Sixth Exemplary Embodiment

In the press plate 26 according to the sixth exemplary embodiment, operation and advantageous effects can be obtained that are a combination of the operation and advantageous effects obtained by the press plate 26 and the radiographic imaging apparatus 10 according to the first exemplary embodiment, and the operation and advantageous effects obtained by the press plate 26 and the radiographic imaging apparatus 10 according to the fifth exemplary embodiment. Note that similarly to in the press plate 26 according to the sixth exemplary embodiment (and in particular to the side in contact with the chest wall), preferably one of the trapping prevention components 269A to 269C of the press plate 26 according to the fourth exemplary embodiment is applied in the press plate 26 according to a sixth exemplary embodiment.

Seventh Exemplary Embodiment

Explanation follows in the seventh exemplary embodiment of the present invention regarding a modified example of a profile of the slits 26E of the press plate 26 according to the first exemplary embodiment.

Press Plate Configuration

Figure 18:
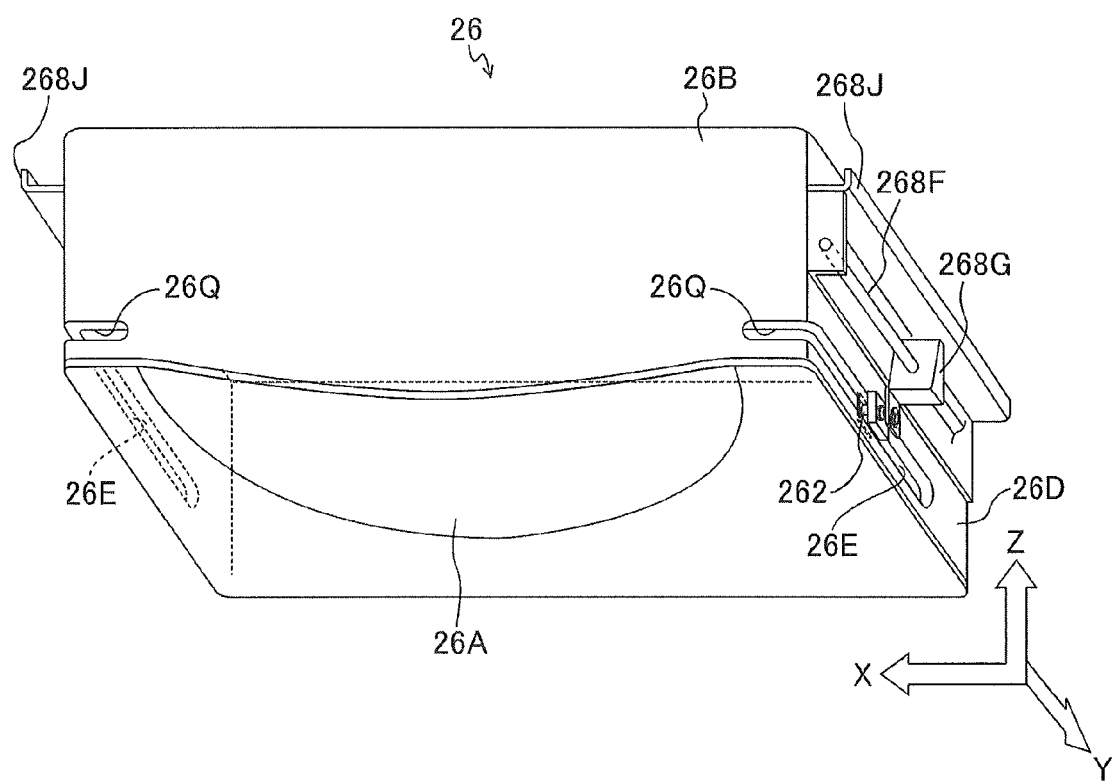
FIG. 18 is a perspective view from the front face side of a press plate of a radiographic imaging apparatus according to a seventh exemplary embodiment of the present invention.

As illustrated in FIG. 18, in a press plate 26 according to the seventh exemplary embodiment, portions at one end at the front face side of slits 26E provided to the side faces respectively extend in the Y direction as far as slits 26Q that are present at a right end portion and a left end portion of the front face of the press plate 26, and are in communication with the slits 26Q. In side view, the coupling section 26C (see FIG. 5) is not provided at the one end side of the slits 26E, and so the press section 26A and the support section 26B are separated from each other at the front face of the press plate 26. Namely, one end side of each of the slits 26E is open. The press section 26A and the support section 26B are coupled together through the coupling section 26D at the other end side of each of the slits 26E. The movable support point portions 262 are movable within the range of the slits 26E.

Operation and Advantageous Effects of the Seventh Exemplary Embodiment

The press plate 26 according to the seventh exemplary embodiment is able to obtain the same operation and advantageous effects at the operation and advantageous effects obtained by the press plate 26 according to the first exemplary embodiment. Moreover, the press plate 26 according to the seventh exemplary embodiment is not provided with the coupling section 26C at the front face side of the press plate 26, but at the rear face side of the press plate 26, the press section 26A and the support section 26B are coupled together by the coupling section 26D, with the front face side of the slits 26E open. The flexibility of the front face side of the press section 26A is accordingly increased, enabling a large deformation amount of the press plate 26 to be adopted. Consequently, pain felt by the examinee W can be reduced even further. Note that, similarly, preferably one of the trapping prevention components 269A to 269C of the press plate 26 according to the fourth exemplary embodiment is applied in the press plate 26 according to the seventh exemplary embodiment (in particular to the side in contact with the chest wall).

Eighth Exemplary Embodiment

Explanation follows regarding an eighth exemplary embodiment of the present invention as a modified example of movement direction of the movable support point portions in the slits 26E of the press plate 26 according to a seventh exemplary embodiment.

Press Plate Configuration

Figure 19A:
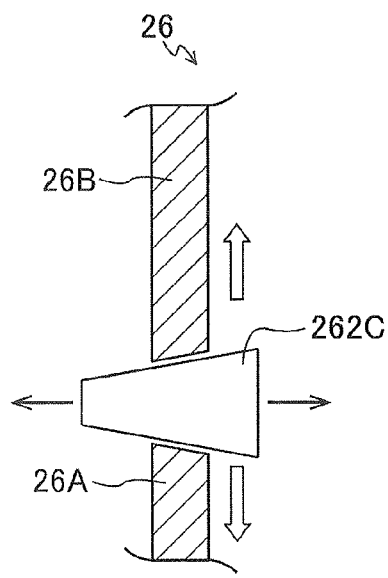
FIG. 19A is an enlarged cross-section of relevant portions viewed from the front face side of a press plate of a radiographic imaging apparatus according to an eighth exemplary embodiment of the present invention.

As illustrated in FIG. 19A, in the press plate 26 according to the eighth exemplary embodiment, in front view (or back view), the movable support point portions 262C are provided with a different external profile dimension at one X direction end to the external profile dimension at the other X direction end. The movable support point portions 262C are each configured with a circular conical shape (tapered circular bar profile) with an external profile dimension that increases on progression at the side face of the press plate 26 from the inside towards the outside (or in the opposite direction thereto). The movable support point portions 262C are movable in a direction (X direction) orthogonal to the extension direction of the slits 26E (the Y direction).

Figure 19B:
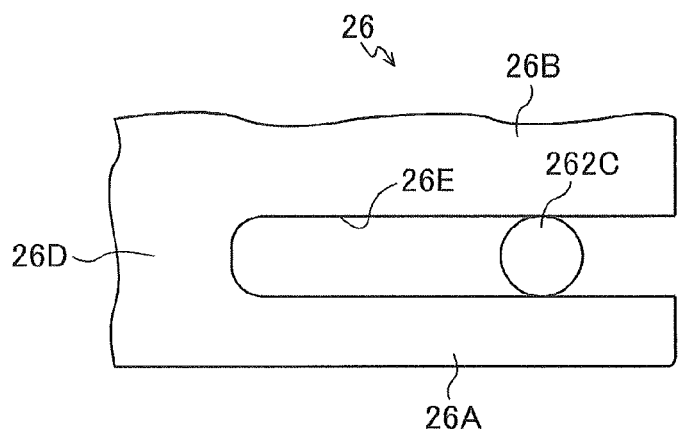
FIG. 19B and FIG. 19C are enlarged side views of relevant portions of the press plate illustrated in FIG. 19A.

As illustrated in FIG. 19B, the movable support point portions 262 move in the X direction, and the press section 26A is supported by the support section 26B through the movable support point portions 262 when the external profile dimension of the movable support point portions 262 is about the width of the slits 26E. In such cases, the press section 26A is deformable according to the distance from this supported position to the front face of the press plate 26.

Figure 19C:
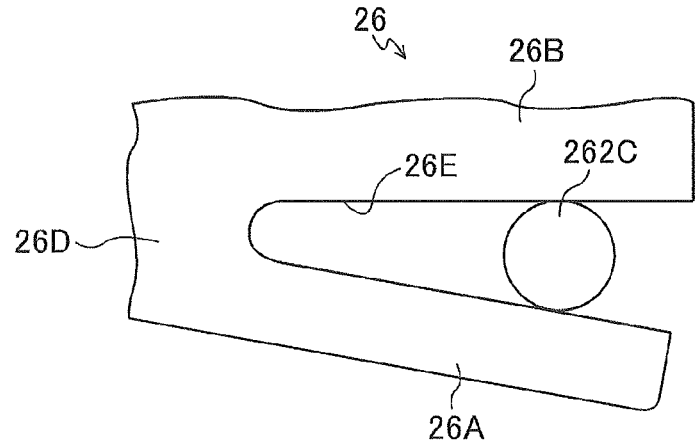

As illustrated in FIG. 19C, when the movable support point portion 262 moves further in the X direction and the external profile dimension of the movable support point portion 262 is larger than the width of the slit 26E, the press section 26A is supported by the support section 26B through the movable support point portions 262, and the press section 26A also separates away from the support section 26B. Namely, within a resiliently deformable range of the coupling section 26D, the press section 26A is pressed out wider downwards centered on the coupling section 26D. In such cases, although it is possible for the press section 26A to deform according to the distance from the support position to the front face of the press plate 26, one end of the front face side of the press section 26A faces downwards, and so deformation upwards (in the Z direction) becomes more difficult. The deformation amount of the press section 26A accordingly decreases.

Namely, it is possible to adjust the deformation amount of the front face side of the press section 26A whilst having the same position of the slits 26E by making the movable support point portions 262 movable in both the extension direction of the slits 26E and in an orthogonal direction thereto. Such adjustment may use one or more methods from the list consisting of the breast elasticity derivation method according to the first exemplary embodiment, the mammary gland density derivation method according to the second exemplary embodiment and the radiation transmissivity derivation method according to the third exemplary embodiment.

Operation and Advantageous Effects of the Eighth Exemplary Embodiment

The press plate 26 according to the eighth exemplary embodiment is able to obtain similar operation and advantageous effects to the operation and advantageous effects obtained by the press plate 26 according to any one of the first to the third exemplary embodiments.

Other Exemplary Embodiments

Although plural exemplary embodiments of the present invention have been explained above, the present invention is not limited by the above exemplary embodiments, and various modifications are possible within a scope not departing from the spirit of the present invention. For example, in the present invention, a press plate 26 and a radiographic imaging apparatus 10 may be configured with a structure that is a combination of elements from 2 or more of the first exemplary embodiment to the fifth exemplary embodiment.

Moreover, although X-rays are employed as radiation in the above exemplary embodiments, there is no limitation thereto. The present invention includes at least radiations such as gamma rays, an electron beam, a neutron beam, a proton beam and a heavy particle beam that are used in medical consultation. Moreover, an explanation has been given in the above exemplary embodiments of examples in which the radiographic imaging apparatus and the press plate are applied to mammography equipment and press plate for mammography equipment, however there is no limitation thereto. For example, the present invention may be applied to a press plate that presses a stomach region in order to perform X-ray imaging such as of a gastrointestinal image capture body, or to an X-ray radiographic imaging apparatus incorporating such a press plate.

Due to the present invention being configured as described above, a press plate capable of achieving an optimum deformation amount for the pressed state with the same pressing force, and a radiographic imaging apparatus of the same can be provided.

What is claimed is:

1. A press plate comprising:
   a support section that includes a press section that forms a slit that extends in a first direction and that is resiliently deformable in a second direction that is orthogonal to the first direction through the slit in the second direction; and
   a movable support point portion that is disposed in the slit and that is movable along the slit and that adjusts a deformation amount, due to a resilient deformation, of the press section by changing a position where the movable support point portion supports the press section according to movement positions in a pressed state with the same pressing force.

2. The press plate of claim 1, wherein:
   at least one end portion of the support section is coupled to one end portion of the press section.

3. The press plate of claim 1, wherein:
   the press section and the support section are configured from the same member provided with the slit.

4. The press plate of claim 1, wherein:
   the press section and the support section are formed in a rectangular shape in plan view; and
   the slit is provided in a front face facing towards an investigation subject, or in side faces, or in both the front face and the side faces.

5. The press plate of claim 1, further comprising a trapping prevention component provided to close off an opening of the slit.

6. The press plate of claim 1, wherein the press section comprises a local face profile that projects out towards the imaging face side.

7. The press plate of claim 1, further comprising:
   a drive source that is provided to the support section; and
   a transmission mechanism that transmits drive force of the drive source to the movable support point portion, wherein the movable support point portion is movable according to the drive force transmitted from the drive source through the transmission mechanism.

8. The press plate of claim 7, further comprising:
   a manual adjustment section that is coupled to the transmission mechanism and that imparts drive force that makes the movable support point portion movable separately to the drive force from the drive source.

9. A radiographic imaging apparatus comprising:
   the press plate of claim 7;
   an imaging table that includes an imaging face that faces towards the press section of the press plate;
   a radiation irradiation section that is disposed facing through the press plate towards the imaging table; and
   an imaging apparatus controller that controls the drive force of the drive source to adjust the movement and positioning of the movable support point portion through the transmission mechanism.

10. The radiographic imaging apparatus of claim 9, wherein:
    the imaging apparatus controller adjusts the movement and positioning of the movable support point portion based on at least one type of data among pressed thickness of an image capture body when the image capture body is disposed on the imaging face and is being pressed by the press plate, pressing force of the press plate, radiation transmissivity of the image capture body, and density of human tissue of the image capture body.

11. The radiographic imaging apparatus of claim 10, wherein:
the density of human tissue comprises density of mammary gland density data, and when the density of the mammary gland density data is higher, the movable support portion is moved and positioned so that the deformation amount is larger.

12. The radiographic imaging apparatus of claim 9, wherein:
the support section is disposed on an opposite side of the press section to the imaging face and separated from the imaging face.

13. The press plate of claim 1, further comprising:
a first coupling section for coupling one end portion that is at a front face side of the support section and one end portion that is at a front face side of the press section; and
a second coupling section for coupling a second end portion that is at a rear face side of the support section and a second end portion that is at the rear face side of the press section are coupled together.

14. The press plate of claim 13, wherein the press section and the support section are integrally formed through the first and second coupling sections.

15. The press plate of claim 1, wherein a thickness in the second direction of the support section is greater than a thickness in the second direction of the press section.

16. The press plate of claim 1, further comprising:
a separation portion disposed between the press section and the support section.

* * * * *